United States Patent
Merrill et al.

[11] Patent Number: 5,914,131
[45] Date of Patent: *Jun. 22, 1999

[54] HYDROMORPHONE THERAPY

[75] Inventors: Sonya Merrill, San Jose; Atul D. Ayer, Palo Alto; Navjot Chadha, Fremont; Anthony L. Kuczynski, Mountain View, all of Calif.

[73] Assignee: ALZA Corporation, Palo Alto, Calif.

[*] Notice: This patent is subject to a terminal disclaimer.

[21] Appl. No.: 08/935,223

[22] Filed: Sep. 22, 1997

Related U.S. Application Data

[63] Continuation-in-part of application No. 08/611,294, Mar. 5, 1996, Pat. No. 5,702,725, which is a continuation of application No. 08/271,593, Jul. 7, 1994, Pat. No. 5,529,787.

[51] Int. Cl.⁶ .............................. A61K 9/20; A01N 43/08
[52] U.S. Cl. ............................. 424/473; 424/472
[58] Field of Search ...................... 424/472, 473

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,008,719 | 2/1977 | Theeuwes et al. | 128/260 |
| 4,036,228 | 7/1977 | Theeuwes et al. | 128/260 |
| 4,111,201 | 9/1978 | Theeuwes et al. | 128/260 |
| 4,111,202 | 9/1978 | Theeuwes et al. | 128/260 |
| 4,327,725 | 5/1982 | Cortese et al. | 128/260 |
| 4,464,378 | 8/1984 | Hussain | 424/260 |
| 4,519,801 | 5/1985 | Edgren | 604/892 |
| 4,576,604 | 3/1986 | Guittard et al. | 604/890 |
| 4,612,008 | 9/1986 | Wong et al. | 604/892 |
| 4,844,907 | 7/1989 | Elger et al. | 424/465 |
| 4,844,909 | 7/1989 | Goldie et al. | 424/480 |
| 5,021,053 | 6/1991 | Barclay et al. | 604/892.1 |
| 5,198,229 | 3/1993 | Wong et al. | 424/473 |
| 5,312,389 | 5/1994 | Theeuwes et al. | 604/892.1 |
| 5,326,571 | 7/1994 | Wright et al. | 424/473 |
| 5,529,787 | 6/1996 | Merrill et al. | 424/465 |
| 5,702,725 | 12/1997 | Merrill et al. | 424/472 |

*Primary Examiner*—Peter F. Kulkosky
*Attorney, Agent, or Firm*—Paul L. Sabatine; Michael J. Rafa; Susan K. Thomas

[57] ABSTRACT

A hydromorphone composition, a hydromorphone dosage form and a method for administering hydromorphone are disclosed, indicated for the management of pain.

46 Claims, 10 Drawing Sheets

HYDROMORPHONE THERAPY

CROSS REFERENCE TO RELATED APPLICATIONS

This application is a continuation-in-part of U.S. application Ser. No. 08/611,294 filed Mar. 5, 1996, now U.S. Pat. No. 5,702,725 which application is a continuation of U.S. application Ser. No. 08/271,593 filed Jul. 7, 1994 and now U.S. Pat. No. 5,529,787 issued Jun. 25, 1996.

FIELD OF THE INVENTION

This invention pertains to a novel dosage form comprising hydromorphone for the management of pain. The invention concerns also a novel therapeutic composition comprising hydromorphone indicated for treating pain. The invention relates additionally to a method for the management of pain by administering continuously release-rate controlled doses of hydromorphone over an extended time to produce analgesic therapy.

BACKGROUND OF THE INVENTION

Hydromorphone is an analgesic with its principal therapeutic effect, the relief of pain. The precise mechanism of action of hydromorphone is not medically understood, although it is thought to relate to the existence of hydromorphone receptors in the central nervous system. Generally, the analgesic action of parenterally administered hydromorphone is apparent within fifteen minutes and the onset of action of orally administered hydromorphone is somewhat slower, with analgesia occurring within thirty minutes. In human plasma, the half-life of hydromorphone is about two and one-half hours. Hydromorphone is indicated for the relief of moderate to severe pain, such as pain due to infection, surgery, cancer, trauma, biliary colic, disease, renal colic, myocardial infarction, and burns. A pharmaceutically-acceptable dosage form for oral administering hydromorphone to provide analgesic therapy beyond its short half-life at a controlled-rate over an extended period of time appears to be lacking in the pharmaceutical and medical arts. The pharmacological and medical properties of hydromorphone are known in *Pharmaceutical Sciences*, Remington, 17th Ed., pp. 1099–1044, (1985); and in the *Pharmacological Basis of Therapeutics*, Goodman and Rall, 8th Ed., pp. 485–518, (1990).

The present invention unexpectedly provides both a dosage form comprising hydromorphone and a therapeutic composition comprising hydromorphone for the management of pain. That is, the prior art did not appreciate that hydromorphone, which is a complex chemical 4,5-expoxy-3-hydroxy-17-methyl-morphinan-6-one, comprising five rings substituted with different chemical groups, can be made into a continuous release dosage form, or into a therapeutic composition. The prior did not appreciate a dosage form and a therapeutic composition can be made available comprising an osmogel such as a polyalkylene oxide and other ingredients including an osmagent. The prior art did not make obvious hydromorphone formulated with a polyalkylene oxide, as the mechanism which controlled the release of hydromorphone from polyalkylene oxide are complex polymers. For example, the hydromorphone could become immobile and trapped in the polyalkylene oxide, also, the polyalkylene oxide could exhibit unacceptable swelling in the presence of aqueous including biological fluid and thereby change the rate of release of the hydromorphone from the polyalkylene oxide. Further, the osmogel such as polyalkylene oxide, can possess a glass-transition temperature below human body temperature, which leads away from using hydromorphone in such an environment. Additionally, the properties of hydromorphone and polyalkylene oxide, exemplified by the crystallinity of hydromorphone in polyalkylene oxide, the burst or lag effect of hydromorphone in polyalkylene oxide, the hydromorphone solubility in a polyalkylene oxide hydrogel all attest to the nonobviousness of the present invention.

Prior to this invention, hydromorphone was administered in conventional forms, such as a nonrate-controlling dose-dumping tablet or by a dose-dumping capsule, and usually at multiple, repetitive dosing intervals. This prior-art mode of therapy leads to an initial high dose of hydromorphone in the blood, followed by a decreased dose of hydromorphone in the blood. The concentration differences in dosing patterns are related to the presence and absence of administered drug, which is a major disadvantage associated with conventional dosage forms. Conventional dosage forms and their mode of operation, including dose peaks and valleys, are discussed in *Pharmaceutical Sciences*, Remington, 18th Ed., pp 1676–1686, (1990), Mark Publishing Co.; *The Pharmaceutical and Clinical Pharmacokinetics*, 3rd Ed., pp 1–28, (1984), Lea and Febiger, Philadelphia.; and in U.S. Pat. Nos. 3,598,122 and 3,598,123, both issued to Zaffaroni.

The above presentation dictates of the critical need for a dosage form and for a therapeutic composition that overcomes the shortcomings of conventional dosage forms, including tablets, capsules, elixirs and suspensions. These conventional dosage forms and their accompanying peaks and valleys do not provide for dose-regulated drug therapy over an extended period of time. The hydromorphone as delivered by the prior art is often dosed two or more times a day, which does not lend itself to controlled and sustained therapy. This prior-art pattern of drug administration speaks of the need for a dosage form and for a therapeutic composition that can administer hydromorphone in a rate-controlled dose over an extended time to provide constant therapy, and thereby eliminate the peaks, valleys, and multiple uncontrolled dosing of the prior art.

In view of the foregoing presentation, it is immediately apparent that a serious need exists for an improvement in the delivery of hydromorphone for its therapeutic analgesic effect. The need exists to provide a novel therapeutic composition comprising hydromorphone, and the need exists to provide a novel method of administering hydromorphone to a patient in need of hydromorphone therapy. The invention provides an oral, relatively-easy to administer mode and manner of hydromorphone therapy.

OBJECTS OF THE INVENTION

Accordingly, in view of the above presentation it is an immediate object of this invention to provide a dosage form and a therapeutic composition for delivering hydromorphone for pain relief, which dosage form and therapeutic composition overcome the shortcomings known to the prior art.

Another object of the present invention is to make available to the medical-pharmaceutical art a dosage form that delivers a member selected from the group consisting of hydromorphone and its pharmaceutically acceptable salts in a sustained-release dosage program over time.

Another object of the invention is to provide a novel dosage form for administering hydromorphone to a patient at a controlled rate and in a continuous dose over time.

Another object of the invention is to provide a therapeutic composition comprising an orally administrable solid hydromorphone comprising an osmopolymer that can be administered as an oral, solid therapeutic composition or administered from an osmotic dosage form comprising the solid initially dry therapeutic composition.

Another object of the invention is to provide a pharmaceutically acceptable composition comprising a member selected from the group consisting of hydromorphone and its pharmaceutically acceptable salts for the relief of moderate to severe pain due to surgery, cancer, trauma, tissue, bone, colic, myocardial infarction, burns and rectal pain in a human patient.

Another object of the invention is to provide a therapeutic composition comprising hydromorphone and an osmotic attractant for delivering a known concentration per unit time for hydromorphone therapy.

Another object of the invention is to provide a hydromorphone formulation that delivers, in a controlled-continuous releasing dose, hydromorphone to a patient in need of hydromorphone therapy for maintaining a hydromorphone level in the blood as a function of the hydromorphone releasing formulation.

Another object of the invention is to provide both a novel dosage form and a novel dosage composition, which in both form, delivers hydromorphone as an analgesic to relieve pain by altering the psychological response to pain and suppress anxiety and apprehension in a patient.

Another object of the invention is to provide a method for administering hydromorphone to a patient for lessening a patient's pain.

Another object of the invention is to make available a composition comprising hydromorphone blended with a pharmaceutically acceptable polymer and an osmotically active agent.

Another object of the invention is to provide a dosage form comprising an external coat comprising hydromorphone for immediate hydromorphone therapy.

Another object of the invention is to provide a dosage form that delivers hydromorphone that reduces and/or eliminates the unwanted influences of a gastrointestinal environment on the delivery of hydromorphone from the dosage form in the gastrointestinal tract of a human.

Other objects, features and advantages of the invention will be more apparent to those versed in the dispensing art, and from the accompanying detailed specification, then in conjunction with the accompanying claims.

BRIEF DESCRIPTION OF THE DRAWING

The drawing figures are not drawn to scale, and are set forth to illustrate various embodiments of the invention. The drawing figures are as follows.

Drawing

Drawing

Drawing

Drawing

Drawing

Drawing

Drawing

In the drawing figures and in the specification, like parts in related figures are identified by like numbers. The terms appearing earlier in the specification and in the description of the drawing figures, as well as embodiments thereof, are further described elsewhere in the disclosure.

DETAILED DESCRIPTION OF DRAWINGS

Figure 1:
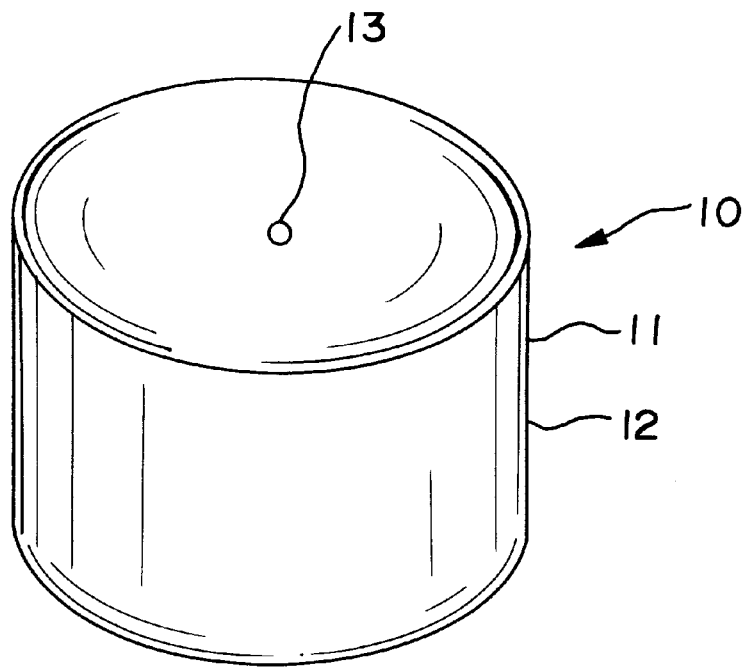
FIG. 1 is a general view of a dosage form provided by this invention, designed and shaped for the oral administration of hydromorphone at a controlled rate over an extended time to a patient in need of hydromorphone therapy.

Turning now to the drawing figures in detail, which drawing figures are examples of a dosage form and a therapeutic composition provided by this invention, and which examples are not to be construed as limiting, one example of a dosage form is seen in drawing FIG. 1. In drawing FIG. 1, a dosage form 10 is seen comprising a body member 11 that comprises a wall 12. Wall 12 is an exterior wall, and it surrounds and defines an internal area, or compartment, not seen in drawing FIG. 1. Dosage form 10 comprises at least one exit 13 that connects an exterior environment, such as the gastrointestinal tract of a human, with the interior of dosage form 10.

Figure 2:
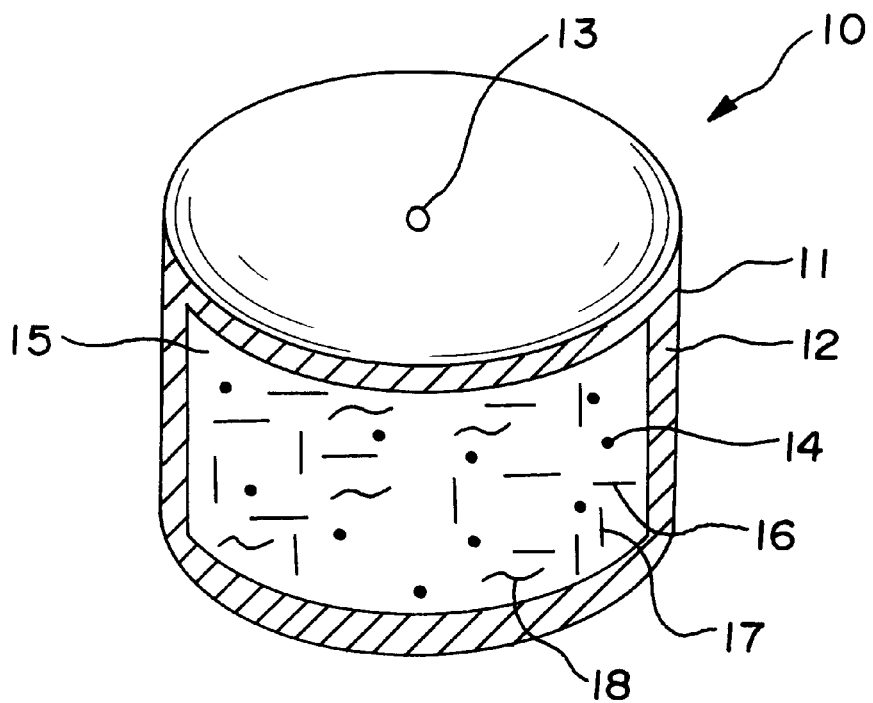
FIG. 2 is a general view of the dosage form of drawing FIG. 1, in opened section, depicting a dosage form of the invention comprising an internally housed, pharmaceutically-acceptable therapeutic hydromorphone composition.

Dosage form 10 of drawing FIG. 2 illustrates a dosage form comprising controlled-release delivery kinetics that delivers a member selected from the group consisting of hydromorphone and its pharmaceutically acceptable salts. The phrase "controlled-release" denotes that dosage form 10 controls or governs the delivery of hydromorphone 14, represented by dots, from internal space or compartment 15. The controlled-release also denotes the delivery of hydromorphone is at a known rate per unit time, over an extended time or thirty-minutes up to twenty-four hours. Dosage form 10, as provided by this invention, is useful for establishing therapeutic hydromorphone therapeutic levels in the blood, including plasma, as a analgesic or pain-lessening therapy. Dosage form 10 as seen in FIG. 2, embraces the shape of a dosage tablet, and it could embrace the shape of a caplet and other oral, buccal, or sublingual dosage forms. The extended-continuous delivery time for the sustain-release dosage form 10, provided by the invention, denotes a sustained-release delivery time greater than conventional, noncontrolled tablets, and noncontrolled, nonsustained-release capsules that exhibit a dose-dumping of their drug.

In drawing FIG. 2, dosage form 10 is seen in opened-section with a section of wall 12 removed for illustrating the internal area 15 of dosage form 10. In drawing FIG. 2, dosage form 10 comprises body 11, wall 12, exit 13 and internal area or compartment 15. Wall 12, which surrounds and defines internal compartment 15, comprised totally or in at least a part, a semipermeable composition. The phrase "semipermeable composition: denotes that the semipermeable composition is permeable to the passage of an exterior fluid, such as aqueous and biological fluid, in the environment of use, including the gastrointestinal tract. Wall 12 is impermeable to hydromorphone, represented by dots 14, present in compartment 15. Wall 12 is nontoxic, inert, and it maintains its physical and chemical integrity during the dispensing life of hydromorphone. Wall 12 comprises a composition that does not adversely effect an animal, a human, or components of the dosage form. Wall 12, in one embodiment, comprises a member selected from the group consisting of a cellulose ester polymer, a cellulose ether polymer and a cellulose ester-ether polymer. These cellulosic polymers have a degree of substitution (DS) on the anhydroglucose unit, from greater than zero up to three inclusive. By "degree of substitution" is meant that the average number of hydroxyl groups originally present on the anhydroglucose unit comprising the cellulose polymer that are replaced by a substituting group. Representative wall 12 polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. Exemplary polymers include cellulose acetate having a DS up to 1 and an acetyl content up to 21%; cellulose acetate having a DS of 1 to 2 and an acetyl content of 21 to 35%; cellulose acetate having a DS of 2 to 3 and an acetyl content of 35 to 44.8%. More specific cellulosic polymers comprise cellulose propionate having a DS of 1.8 and a propyl content of 39.2 to 45% and a hydroxy content of 2.8 to 5.4; cellulose acetate butyrate having a DS of 1.8, and acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7; cellulose triacylates having a DS of 2.9 to 3, such as cellulose trivalerate, cellulose trilaurate, cellulose tripalmitate, cellulose trisuccinate, and cellulose trioctanoate; celluloses diacylate having a DS of 2.2 to 2.6, such as cellulose disuccinate, cellulose dipalmitate, cellulose dioctanoate, cellulose dipentanoate, co-esters of cellulose, such as cellulose acetate butyrate, and cellulose acetate propionate. The poly (cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable crosslinked polystyrenes; semipermeable cross-linked poly(sodium styrene sulfonate); semipermeable crosslinked poly(vinylbenzyltrimethyl ammonium chloride); and semipermeable polymers possessing a fluid permeability of $2.5 \times 10^{-8}$ to $2.5 \times 10^{-2}$ (cm$^2$/hr·atm) expressed per atmosphere of hydrostatic or osmotic pressure difference across the semipermeable wall. The polymers are known to the polymer art in U.S. Pat. Nos. 3,845,770; 3,916,899 and 4,160,020; and in *Handbook of Common Polymers*, Scott, J. R. and W. J. Roff, 1971, CRC Press, Cleveland, Ohio.

The drug hydromorphone 14, as seen in drawing FIG. 2, is comprised of: 4,5-epoxy-3-hydroxy-17-methylmorphinan-6-one, possessing analgesic therapy. Hydromorphone is known in *The Merck Index*, 11th Ed., p. 762 (1990). Representative of hydromorphones 14 for this invention comprise a member selected from the group consisting of hydromorphone and its pharmaceutically acceptable salt. The hydromorphone salts are represented by a member selected from the group consisting of the following: hydromorphone sulfate, hydromorphone hydrochloride, hydromorphone trifluoracetate, hydromorphone thiosemicarbazone hydrochloride, hydromorphone pentafluoropropionate, hydromorphone p-nitrophenylhydrozone, hydromorphone hydrazine, hydromorphone hydrobromide, hydromorphone mucate, hydromorphone methylbromide, hydromorphone oleate, hydromorphone n-oxide, hydromorphone acetate, hydromorphone phosphate dibasic, hydromorphone phosphate monobasic, hydromorphone inorganic salt, hydromorphone organic salt, hydromorphone acetate trihydrate, hydromorphone bis (heptafluorobutyrate), hydromorphone bis (methylcarbamate), hydromorphone (bis-pentafluoropropionate), hydromorphone bis(pyridine-3-carboxylate), hydromorphone bis(trifluoroacetate), hydromorphone bitartrate, hydromorphone chlorohydrate, and hydromorphone sulfate pentahydrate. The dosage form and the therapeutic composition in either manufacture comprises 1 mg to 500 mg of hydromorphone 14 or hydromorphone 14 pharmaceutically acceptable salt.

The hydromorphone composition provided by the present invention comprises hydromorphone 14 blended with a pharmaceutically acceptable hydrogel polymer 16, represented by dashes. Representative polymer hydrogels comprise a maltodextrin polymer comprising the formula $(C_6H_{12}O_5)_\lambda \cdot H_2O$, wherein $\lambda$ is 3 to 7,500, and the maltodextrin polymer comprises a 500 to 1,250,000 number-average molecular weight; a poly(alkylene oxide) represented by a poly(ethylene oxide) and a poly(propylene oxide) having a 50,000 to 750,000 weight-average molecular weight, and more specifically represented by a poly (ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight. The therapeutic composition comprises 20 to 375 mg of a polymer hydrogel. The therapeutic composition can be manufactured into dosage form 10, and or can be used as the therapeutic composition for its therapeutic effect.

Dosage form 10 comprises a therapeutically acceptable vinyl polymer represented by vertical dashes 17. The vinyl polymer comprises a 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinylcaprolactone, poly-n-vinyl-5-methyl-2-pyrrolidone, and poly-n-vinyl-pyrrolidone copolymers with a member selected from the group consisting of vinyl acetate, vinyl alcohol, vinyl chloride, vinyl fluoride, vinyl butyrate, vinyl laureate, and vinyl stearate. The dosage form 10, and the therapeutic composition comprises 0.01 to 25 mg of the binder or vinyl polymer, that serves as a binder. Representative of other binders include: acaia, starch, gelatin, and hydroxypropylalkylcellulose of 9,200 to 250,000 molecular weight.

The dosage form comprises a lubricant 18 represented by a wavy line. The lubricant is used during manufacture to prevent sticking to die walls or punch faces. Typical lubricants include: magnesium stearate, sodium stearate, stearic acid, calcium stearate, magnesium oleate, oleic acid, potassium oleate, caprylic acid, sodium stearyl fumarate, and magnesium palmitate. The amount of lubricant present in the therapeutic composition is 0.01 mg to 10 mg.

Figure 3:
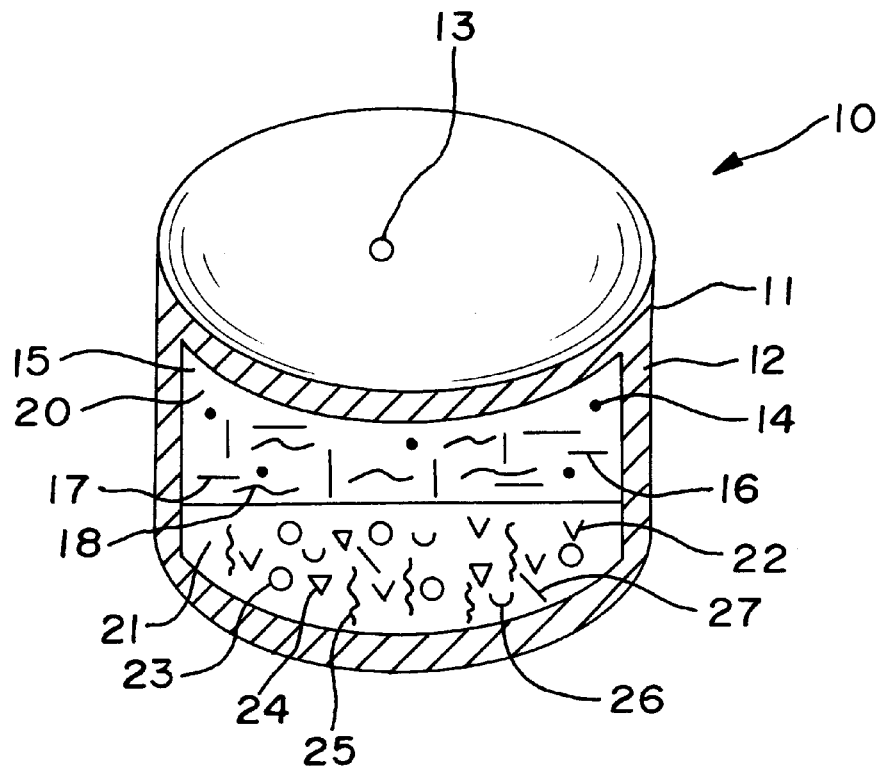
FIG. 3 is an opened view of drawing FIG. 1, illustrating a dosage form internally comprising a hydromorphone composition and a separate and contacting displacement composition comprising means for pushing the pharmaceutical hydromorphone composition form the dosage form.

Drawing FIG. 3 depicts dosage form 10 in opened section, illustrating internal compartment 15. Internal compartment 15 comprises therapeutic composition containing hydromorphone 14, described in detail in drawing FIG. 2. The therapeutic composition of drawing FIG. 2 is identified in drawing FIG. 3 as layer 20 or therapeutic hydromorphone layer 20. Layer 20 comprises the ingredients described in drawing FIG. 2 and the details previously disclosed are included in this description of drawing FIG. 3. Layer 20 in drawing FIG. 3 initially is in contact with expandable layer 21.

Expandable layer 21 comprises 20 mg to 375 mg of an expandable osmopolymer 22, represented by "V". The osmopolymer 22 in layer 21 possesses a higher molecular weight than osmopolymer 16 in the therapeutic hydromorphone composition. The osmopolymer 22 comprises a member selected from the group consisting of a polyalkylene oxide and a carboxyalkylcellulose. The polyalkylene oxide possesses a 1,000,000 to 10,000,000 weight-average molecular weight. Representative of polyalkylene oxide include a member selected from the group consisting of polymethylene oxide, polyethylene oxide, polypropylene oxide, polyethylene oxide having a 1,000,000 molecular weight, polyethylene oxide comprising a 5,000,000 molecular weight, polyethylene oxide comprising a 7,000,000 molecular weight, cross-linked polymethylene oxide possessing a 1,000,000 molecular weight, and polypropylene oxide of 1,200,000 molecular weight. Typical osmopolymer 22 carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The osmopolymers used for the expandable layer exhibit an osmotic pressure gradient across semipermeable wall 12. The osmopolymers imbibe fluid into dosage form 10, thereby swelling and expanding as an osmotic hydrogel (also known as osmogel) whereby, they push the hydromorphone from the osmotic dosage form. The amount of osmopolymer 22 in expandable layer 21 is 20 to 375 mg.

Expandable layer 21 comprises 0 to 75 mg and presently 5 to 75 mg of an osmotically effective compound 23, represented by circles. The osmotically effective compounds are known also as osmagents and as osmotically effective solutes. They imbibe an environmental fluid, for example, from the gastrointestinal tract, into dosage form 10, for contributing to the delivery kinetics of expandable layer 21. Representative of osmotically active compounds comprise a member selected from the group consisting of osmotic salts, and osmotic carbohydrates. Representative of specific osmagents include sodium chloride, potassium chloride, magnesium sulfate, lithium phosphate, lithium chloride, sodium phosphate, potassium sulfate, sodium sulfate, potassium phosphate, glucose, fructose and maltose.

Expandable layer 21 comprises 1 to 75 mg of a hydropropylalkyl cellulose, represented by triangles. The hydroxypropylalkylcellulose possesses a 9,000 to 450,000 number-average molecular weight. The hydroxypropylalkylcellulose is represented by a member selected from the group consisting of hydroxypropylmethylcellulose, hydroxypropylethylcellulose, hydroxypropylisopropylcellulose, hydroxypropylbutylcellulose, and hydroxypropylpentylcellulose. Expandable layer 21 optionally comprises a hydroxyalkylcellulose, also represented by triangles. The hydroxyalkylcellulose comprises a member selected from the group consisting of hydroxymethylcellulose, hydroxyethylcellulose, hydroxypropylcellulose, and hydroxybutylcellulose comprising a 7,500 to 150,000 vicosity-average molecular weight. The amount of hydroxyalkylcellulose in the layer is 0.00 mg to 40 mg.

Expandable layer 21 comprises 0 to 5 mg of a nontoxic colorant or dye 25, identified by vertical wave lines. Colorant 25 includes Food and Drug Administration Colorant (FD&C), such as FD&C No. 1 blue dye, FD&C No. 4 red dye, red ferric oxide, yellow ferric oxide, titanium dioxide, carbon black, and indigo. A lubricant 26, identified by half circles, is formulated into expandable layer 21. Typical lubricants, comprise a member selected from the group consisting of sodium stearate, potassium stearate, magnesium stearate, stearic acid, calcium stearate, sodium oleate, calcium palmitate, sodium laurate, sodium ricinoleate, and potassium linoleate. The concentrate of lubricant is 0.01 to 10 mg.

An antioxidant 27, represented by slanted dashes, is present in expandable formulation 21 to inhibit the oxidation of ingredients comprising expandable formulation 21. Expandable formulation 21 comprises 0.00 to 5 mg of an antioxidant. Representative antioxidants comprise a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alphatocopherol, and propylgallate.

Figure 4:
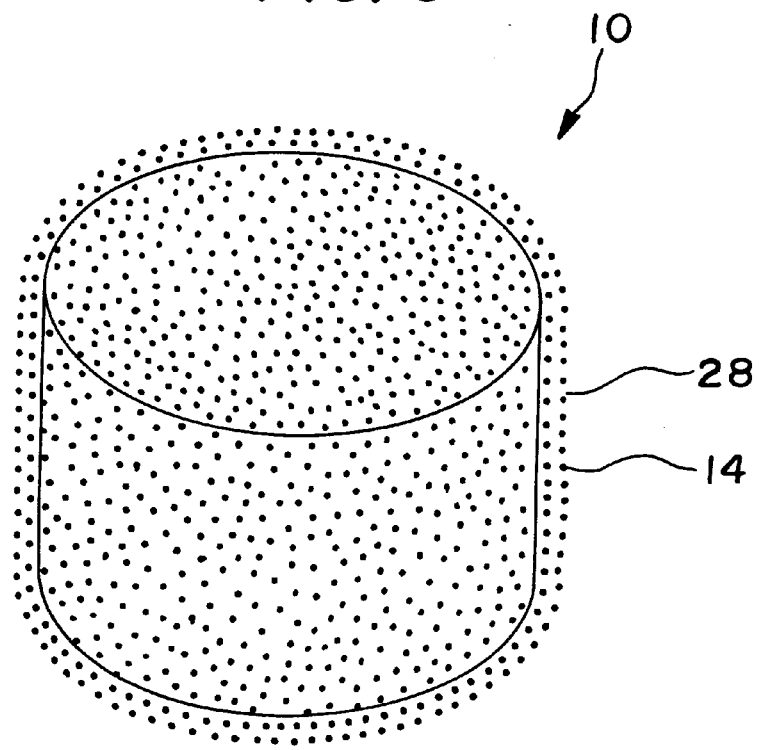
FIG. 4 is a view of a dosage form provided by this invention, which dosage form is illustrated comprising an instant-release external overcoat on the dosage form, which overcoat comprises an instant dose of hydromorphone for the lessening of pain.

Dosage form 10, as seen in drawing FIG. 4, depicts another manufacture provided by the invention. Dosage form 10 comprises an overcoat 28 on the outer surface of wall 12 of dosage form 10. The overcoat 28 is a therapeutic composition comprising 0.5 to 75 mg of hydromorphone 14 and 0.5 to 275 mg of a pharmaceutically acceptable carrier selected from the group consisting of alkylcellulose, hydroxyalkylcellulose and hydroxypropylalkylcellulose. The overcoat is represented by methylcellulose, hydroxyethylcellulose, hydroxybutylcellulose, hydroxypropylcellulose, hydroxypropylmethylcellulose, hydroxypropylethylcellulose and hydroxypropylbutylcellulose. Overcoat 28 provides therapy immediately as overcoat 28 dissolves or undergoes dissolution in the presence of gastrointestinal fluid and concurrently therewith delivers hydromorphone 14 into the gastrointestinal tract for immediate hydromorphone therapy.

Dosage form 10, manufactured as an osmotically controlled-release dosage form, comprises at least one passageway 13. The phrase "controlled-release" as used herein indicates that control is exercised over both the duration and the profile of the hydromorphone release pattern. The expression "passageway" as used for the purpose of this invention, includes aperture, orifice, bore, pore, porous element through which hydromorphone drug 14 can be pumped, diffuse or migrate through a fiber, capillary tube, porous overlay, porous insert, microporous member, and porous composition. The passageway 13 includes also a compound that erodes or is leached from wall 12 in the fluid environment of use to produce at least one passageway. Representative compounds for forming a passageway include erodible poly(glycolic) acid, or poly(lactic) acid in the wall; a gelatinous filament; a water-removable poly (vinyl alcohol); leachable compounds such as fluid-removable pore-forming polysaccharides, acids, salts or oxides. A passageway can be formed by leaching a compound from wall 12, such as sorbitol, sucrose, lactose, maltose, or fructose, to form a controlled-release dimensional pore-passageway. The passageway can have any shape, such as round, triangular, square and elliptical, for assisting in the controlled metered release of hydromorphone 14 from the dosage form. The dosage form can be manufactured with one or more passageways in spaced-apart relation on one or more surfaces of the dosage form. A passageway and equipment for forming a passageway are disclosed in U.S. Pat. Nos. 3,845,770 and 3,916,899 by Theeuwes and Higuchi; in U.S. Pat. No. 4,063,064 by Saunders et al.; and in U.S. Pat. No. 4,088,864 by Theeuwes et al. Passageways comprising controlled-release dimensions sized, shaped and adapted as a releasing-pore formed by aqueous leaching to provide a releasing-pore of a controlled-release rate are disclosed in U.S. Pat. Nos. 4,200, 098 and 4,285,987 by Ayer and Theeuwes.

PROCESS FOR PROVIDING THE INVENTION

Wall 12 of dosage form 10 is manufactured in one process comprising an air suspension process. This process consists in suspending and tumbling a compressed drug core comprising a single-layered core or a bilayered core in a current of air and wall-forming composition until a wall is applied to the single-layered core or the bilayered core. The air suspension procedure is well suited for independently forming the wall. The air suspension procedure is described in U.S. Pat. No. 2,799,241; *J Amer Pharm Assoc*, Vol. 48, pp. 451–454 (1959); and ibid.; Vol. 49, pp. 82–84 (1960). Dosage form 10 can be coated also with a wall-forming composition in an air suspension coater using a solvent, such as a methylene dichloride-methanol cosolvent comprising 80:20 wt:wt, or an ethanol-water cosolvent, or an acetone-water cosolvent consisting of 95:5 wt:wt using 2.5 to 4% solvents.

An air suspension coater using a methylene dichloride-methanol cosolvent, for example, 80:20 wt:wt, can be used for appyling the wall. Other wall-forming techniques, such as a pan-coating system wherein wall-forming compositions are deposited by successive spraying of the drug-core composition to provide a wall that defines and surrounds a compartment, accompanied by tumbling in a rotating pan. Finally, the wall-coated cores are dried in an oven, forced or nonforced air oven, at 30–50° C. for up to a week to free the dosage form of solvent. The walls formed by these techniques have a thickness of 1 to 30 mils (0.0254 to 0.762 mm).

Dosage form 10 of the invention is manufactured by other manufacturing techniques. For example, in one manufacture the drug and other core-forming ingredients comprising a single drug layer or bilayer core with drug facing the exit means 13 are blended and pressed into a solid layer or a solid bilayer. The drug and other ingredients can be dry-blended or blended with a solvent and mixed into a solid or semisolid formed by conventional methods such as ball-milling, calendaring, stirring, roll-milling, or churning, and can then be pressed into a preselected shape. The layer possesses dimensions that correspond to the internal dimensions of the area the single layer occupies in the dosage form, or in a bilayer where it also possesses dimensions corresponding to the first and second layer for forming a contacting arrangement therewith. In a bilayered core, the push layer is placed in contact with the drug layer. The push layer is manufactured using techniques for providing the drug layer. The layering of the drug layer and the push layer can be fabricated by conventional press-layering techniques. Finally, a single layer or a two-layer compartment forming members are surrounded and coated with an exterior wall. A passageway is provided, such as by laser or mechanically drilled through the wall to contact the drug layer. When the passageway is formed by a laser, the dosage form is optically oriented automatically by the laser equipment for forming the passageway on the preselected surface for forming the passageway.

In another manufacture, dosage form 10 is manufactured by a granulation technique. Granulation is a process of size enlargement whereby small particles are gathered into larger aggregates in which the original particles can still be identified. Granulation can be divided into a dry method, wherein no liquid is used for the aggregation, or into a wet method, wherein a liquid is used for granule agglomeration of powder particles followed by a drying process. Granulation is reported in *Encyclopedia of Pharmaceutical Technology*, Vol. 7, pp.121–160, (1993), published by Marcel Dekker, Inc. In the wet granulation technique, for example, the drug and other ingredients comprising the composition or drug-forming layer, or the drug-forming expandable bilayer core are blended using a solvent, such as ethyl alcohol-water 98:2 v:v (volume:volume) as the granulation fluid. Other granulating fluid, such as denatured alcohol 100%, can be used for this purpose. The ingredients forming the drug core or bilayers are individually passed through a mesh screen, such as a U.S. Sieve Series screen, and then thoroughly blended in a mixer. Other ingredients comprising the layer or layers are dissolved in a portion of the granulation fluid, such as the cosolvent described above. Then, the latter prepared wet blend is added slowly to the drug blend with continual mixing in the blender. The granulating fluid is added until a wet blend is produced, which wet mass is then forced through a mesh screen onto oven trays. The blend is dried for 18 to 24 hours at 30–50° C. The dry granules are then sized with a mesh screen. Next, a lubricant is passed through a screen and added to the dry screen granule blend. The granulation is placed in a blender and blended for 1 to 15 minutes. A push layer is made by the same wet granulation, which consists in suspending and tumbling the two contacting layers in a current of air until the wall-forming composition surrounds the layers. The air suspension procedure is described in U.S. Pat. No. 2,799, 241; *J Amer Pharm Assoc*, Vol. 48, pp. 451–454 (1979); and ibid., Vol. 49, pp. 82–84 (1960). Other standard manufacturing procedures are described in *Modern Plastics Encyclopedia*, Vol. 46, pp. 62–70 (1969); and *Pharmaceutical Sciences*, Remington, 14th Ed., pp. 1626–1678 (1970), Mack Publishing Co., Easton, Pa. Granulation techniques are described in ibid., pp. 1655–1660 (1970).

Exemplary solvents suitable for manufacturing the wall, a single layer and a bilayer include inert inorganic and organic solvents. The solvents include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone, alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclooctane, benzene, toluene, naphtha, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DESCRIPTION OF EXAMPLES OF THE INVENTION

The following examples are illustrative of the present invention and they should not be considered as limiting the scope of the invention in any way, as these examples and other equivalents thereof will become apparent to those versed in the art in light of the present disclosure, drawings and accompanying claims.

EXAMPLE 1

A novel therapeutic composition comprising hydromorphone, wherein the hydromorphone is a member selected from the group consisting of hydromorphone pharmaceutically acceptable base and hydromorphone pharmaceutically acceptable salt, is prepared as follows: First, 175 g of hydromorphone hydrochloride, 647.5 g of poly(ethylene oxide) possessing a 200,000 molecular weight, and 43.75 g of poly(vinyl pyrrolidone) having an average-molecular weight of 40,000 are added to planetary mixing bowl and the ingredients dry mixed for ten minutes. Then, 331 g of denatured anhydrous alcohol is slowly added to the blended ingredients, with continuous blending for approximately ten minutes. Next, the freshly prepared wet granulation is passed through a 20-mesh screen, allowed to dry at 25° C. for about 20 hours, and then passed through a 16-mesh screen. Next, the granulation is transferred to the planetary mixer and lubricated with 8.75 g of magnesium stearate to produce a therapeutic hydromorphone composition. The composition is compressed into tablets comprising 35 mg of hydromorphone hydrochloride. The tablets are compressed under 8.5 tons of pressure to provide extended-release hydromorphone hydrochloride tablets.

EXAMPLE 2

The therapeutic compositions manufactured by following the above example provide compositions comprising 1 to 500 mg of a member selected from the group consisting of hydromorphone, hydromorphone base, hydromorphone salt and hydromorphone derivative; at least one polymeric carrier for the hydromorphone selected from 20 to 375 mg of poly(alkylene oxide) comprising a 50,000 to 750,000 molecular weight represented by poly(methylene oxide), poly(ethylene oxide), poly(propylene oxide), poly(isopropylene oxide) and poly(butylene oxide), or a polymeric carrier for the hydromorphone consisting of 20 to 375 mg of carboxymethylcellulose having a 10,000 to 175,000 molecular weight represented by a member selected from the group consisting of alkali carboxymethylcellulose, sodium carboxymethylcellulose and postassium carboxymethylcellulose; 0.01 to 25 mg of poly(vinyl) polymer possessing a 5,000 to 350,000 molecular weight represented by poly(vinyl pyrrolidone), copolymer of poly(vinyl pyrrolidone and vinyl acetate), copolymer of poly(vinyl pyrrolidone and vinyl alcohol), copolymer of poly(vinyl pyrrolidone and vinyl chloride), copolymer of poly(vinyl pyrrolidone and vinyl fluoride), copolymer of poly(vinyl pyrrolidone and vinyl butyrate), copolymer of poly(vinyl pyrrolidone and vinyl laureate), and copolymer of poly(vinyl pyrrolidone with vinyl stearate); and 0 to 10 mg of a lubricant represented by a member selected from the group consisting of magnesium stearate, calcium stearate, potassium oleate, sodium stearate, stearic acid and sodium palmitate. The therapeutic composition may contain other ingredients, for example, colorants, compression aids and binders. The composition can be compressed at ¼ to 10-ton force to yield an orally administrable tablet comprising hydromorphone.

EXAMPLE 3

The therapeutic composition provided by the invention can be dry compressed into an orally administrable dosage form. For example, a mixture of dry-powder ingredients comprising a hydromorphone pharmaceutically acceptable base or a hydromorphone pharmaceutically acceptable salt as represented by: hydrochloride, hydrobromide, sulfate, bisulfate, acetate, valerate, oxalate, oleate, laureate, borate, benzoate, lactate, phosphate, tosylate, citrate, maleate, fumarate, succinate, tartrate and napsylate; a tablet excipient represented by 0 to 200 mg of microcrystalline cellulose; 20 to 375 mg of sodium carboxymethylcellulose of 10,000 to 175,000 molecular weight; 0.01 to 25 mg of a binder agent represented by poly(vinyl pyrrolidone) of 5,000 to 350,000 molecular weight, a hydroxypropylmethylcellulose of 9,200 to 75,000 molecular weight, and gelatin; and 0 to 10 mg of a lubricant, such as stearic acid, calcium stearate or magnesium stearate; are dried, sieved and mixed with other optional ingredients, such as a surfactant and a flavoring agent, then fed to a tablet press and compressed to yield dry-compressed hydromorphone tablets for oral administration to a patient in need of hydromorphone analgesic pain relief. In a manufacture provided by the invention a therapeutic composition made by wet-granulation or dry-granulation processes can be surrounded with a semipermeable, polymeric wall. The semipermeable wall is pervious to fluid, impervious to hydromorphone, and an exit means, such as a passageway through the semipermeable wall, provides for the delivery of hydromorphone at a controlled-sustained rate through the exit means over time.

EXAMPLE 4

A dosage form, adapted, designed and shaped as an osmotic drug delivery device is manufactured as follows: First, 175 g of hydromorphone hydrochloride, 647.5 g of poly(ethylene oxide) possessing a 200,000 molecular weight, and 43.75 g of poly(vinyl pyrrolidone) having a 40,000 molecular weight are added to a mixer and mixed for ten minutes. Then, 331 g of denatured anhydrous alcohol is added to the blended materials, with continuous mixing for ten minutes. Then, the wet granulation is passed through a 20-mesh screen, allowed to dry at room temperature for 20 hours, and then passed through a 16-mesh screen. Next, the granulation is transferred to the mixer, mixed, and lubricated with 8.75 g of magnesium stearate.

Then, a displacement or push composition for pushing the therapeutic hydromorphone composition from the dosage form is prepared as follows: First, 3910 g of hydroxypropylmethylcellulose possessing a 11,200 molecular weight is dissolved in 45,339 g of water. Then, 101 g of butylated hydroxytoluene is dissolved in 650 g of denatured anhydrous alcohol. Next, 2.5 kg of the hydroxypropylmethylcellulose aqueous solution is added, with continuous mixing, to the butylated hydroxytoluene alcohol solution. Then, the binder solution preparation is completed by adding, with continuous mixing, the remaining hydroxypropylmethylcellulose aqueous solution to the butylated hydroxytoluene alcohol solution.

Next, 36,000 g of sodium chloride is sized using a mill equipped with a 21-mesh screen. Then, 1200 g of ferric oxide is passed through a 40-mesh screen. Then, the screened materials, 76,400 g of pharmaceutically acceptable poly(ethylene oxide) possessing a 7,500,000 molecular weight, and 2500 g of hydroxypropylmethylcellulose having a 11,200 molecular weight are added to the bowl of a fluid bed granulator. The bowl is attached to the granulator and the granulation process is initiated for effecting granulation. Next, the dry powders are air suspended and mixed for ten minutes. Then, the binder solution is sprayed from three nozzles onto the powder. The granulating is monitored during the process as follows: total solution spray rate of 800 g/min; inlet temperature of 43° C.; and an air flow of 4300 $m^3$/hr. At the end of the solution spraying process, 45,033 g of the coated, granulated particles are dried for 35 minutes at room temperature. The granules are sized using a mill with a 8-mesh screen. The granulation is transferred to a tumbler, mixed, and lubricated with 281.7 g of magnesium stearate.

Next, the drug composition comprising the hydromorphone hydrochloride and the push composition is compressed into bilayer tablets on a tablet press. First, 176 mg of the hydromorphone hydrochloride composition is added to the die cavity and precompressed. Then, 135 mg of the push composition is added, and the layers are pressed under a pressure head of 3-metric tons into a 11/32 in. (0.873 cm) diameter, contacting layer arrangement.

The bilayered arrangements are coated with a semipermeable wall. The wall-forming composition comprises 100% cellulose acetate having a 39.8% acetyl content. The wall-forming composition is dissolved in acetone:water (95:5 wt:wt) cosolvent to make a 4%-solid solution. The wall-forming composition is sprayed onto and around the bilayers in a 24-inch coater.

Next, one 20 mil (0.508 mm) exit passageway is drilled through the semipermeable wall to connect the drug hydromorphone layer with the exterior of the dosage form. The residual solvent is removed by drying for 72 hours at 45° C. and 45% humidity. Next, the osmotic dosage systems are dried for four hours at 45° C. to remove excess moisture. The dosage form produced by this manufacture comprises 35.20 mg of hydromorphone hydrochloride, 130.24 mg of poly(ethylene oxide) of 200,000 molecular weight, 8.80 mg of poly(vinyl pyrrolidone) of 40,000 molecular weight, and 1.76 mg of magnesium stearate. The push composition comprises 85.96 mg of poly(ethylene oxide) of 7,500,000 molecular weight, 40.50 mg of sodium chloride, 6.75 mg of hydroxypropylmethylcellulose, 1.35 mg of red ferric oxide, 0.34 mg of magnesium stearate, and 0.10 mg of butylated hydroxytoluene. The semipermeable wall comprises 38.6 mg of cellulose acetate comprising a 39.8% acetyl content. The dosage form comprises one 20 mil (0.508 mm) passageway, and the dosage form has a hydromorphone hydrochloride mean release rate of 1.6 mg/hr over an extended period of 28 hours.

EXAMPLE 5

The procedure of Example 4 is followed, with all manufacturing procedures as described, except in this example the hydroxypropylmethylcellulose is replaced by a hydroxypropylmethylcellulose having a 300,000 molecular weight.

EXAMPLE 6

The procedure of Example 4 is followed, with all manufacturing procedures as described, except in this example the poly(ethylene oxide) in the hydromorphone drug composition is replaced by a sodium carboxymethylcellulose possessing a 175,000 molecular weight, and the poly(ethylene oxide) in the push composition is replaced by a sodium carboxymethylcellulose possessing a 700,000 molecular weight. In an inventive embodiment, the alkali carboxymethylcellulose present in the push composition possesses a greater molecular weight than the alkali carboxymethylcellulose of the hydromorphone drug composition.

EXAMPLE 7

The dosage form prepared by the above examples can be manufactured with a semipermeable wall composition comprising 65 to 100 wt % of a cellulose polymer comprising a member selected from the group consisting of: cellulose ester, cellulose diester, cellulose triester, cellulose ether, cellulose ester-ether, cellulose acylate, cellulose diacylate, cellulose triacetate, cellulose acetate butyrate, and the like. The wall can also comprise from 0 to 40 wt % of a cellulose ether selected from the group consisting of: hydroxypropylcellulose, hydroxypropylmethylcellulose, hydroxypropylethylcellulose, hydroxypropylbutylcellulose and hydroxypropylpentylcellulose. The wall can further comprise 0 to 20 wt % of polyethylene glycol. The total amount of all components comprising the wall is equal to 100 wt %. Semipermeable polymers are disclosed in U.S. Pat. Nos. 3,845,000, 3,916,899, 4,008,719, 4,036,228 and 4,111,201. These patents are assigned to the ALZA Corporation of Palo Alto, Calif., the assignee of this patent application.

In another manufacture, the wall can be prepared according to the above examples comprising the selectively permeable cellulose ether: ethyl cellulose. The ethyl cellulose comprises an ethoxy group with a degree of substitution (DS) of about 1.4 to 3, equivalent to 40 to 50% ethoxy content, and a viscosity range of 7 to 100 centipoise or higher. A representative wall comprises 45 to 80 wt % ethylcellulose, from 5 to 30 wt % hydroxypropyl cellulose, and from 5 to 30 wt % polyethylene glycol, with the total amount of all components comprising the wall equal to 100 wt %. In another manufacture, the wall comprises 45 to 80 wt % ethylcellulose, 5 to 30 wt % hydroxypropylcellulose, and 2 to 20 wt % poly(vinyl pyrrolidone). The total amount of all components comprising the wall is equal to 100 wt %. The ethylcellulose polymer is known in U.S. Pat. No. 4,519,801, assigned to the ALZA Corporation of Palo Alto, Calif.

EXAMPLE 8

The dosage form provided by the invention comprises a hydro morphone drug composition consisting of 1 to 500 mg of hydromorphone, hydromorphone base, hydromorphone salt or hydromorphone derivative; at least one of 20 to 375 mg of poly(alkylene oxide) of 50,000 to 750,000 molecular weight, or 25 to 375 mg of a carboxymethylcellulose of 10,000 to 175,000 molecular weight; at least one of 0.01 to 25 mg of a poly(vinyl pyrrolidone) of 5,000 to 350,000 molecular weight, or 0 to 50 mg of a hydroxypropylcellulose or hydroxypropylalkylcellulose of 7,500 to 75,000 molecular weight; and 0.01 to 10 mg of a lubricant, such as magnesium stearate.

The dosage form provided by the invention comprises a push composition consisting of at least one of 20 to 375 mg of a poly(alkylene oxide) of 1,000,000 to 10,000,000 molecular weight, or 20 to 425 mg of a carboxymethylcellulose, such as sodium carboxymethylcellulose, and a potassium carboxymethylcellulose of 200,000 to 7,500,000, molecular weight; 0 to 75 mg of an osmagent, also known as osmotically effective solute, represented by magnesium sulfate, sodium chloride, lithium chloride, potassium sulfate, sodium sulfate, lithium sulfate, potassium acid phosphate, mannitol, urea, inositol, magnesium succinate, tartaric acid, carbohydrates such as raffinose, sucrose, glucose, lactose, fructose, sodium chloride and fructose, potassium chloride and dextrose; 1 to 75 mg of a hydroxyalkyl cellulose selected from the group consisting of hydroethylcellulose, hydroxypropylcellulose, hydroxyisopropylcellulose, hydroxybutylcellulose, hydroxypropylmethylcellulose, hydroxypropylethylcellulose, and hydroxypropylbutylcellulose, which hydroxyalkylcellulose comprises a 9,000 to 450,000 molecular weight; 0 to 10 mg of an antioxidant represented by d-alpha tocopherol acetate, dl-alpha tocopherol, ascorbyl palmitate, butylated hydroxyanisole, butylated hydroxytoluene and propyl gallate; 0 to 10 mg of a lubricant represented by magnesium stearate, calcium stearate, corn starch, potato starch, bentonite, citrus pulp, and stearic acid; and 0 to 10 mg of a colorant.

EXAMPLES 9–12

Dosage forms are provided by following the above procedures comprising the following: (A) A dosage form with a drug layer comprising 8 mg of hydromorphone hydrochloride, 67.8 mg of poly(ethylene oxide) possessing a 200,000 molecular weight, 4 mg of poly(vinyl pyrrolidone) of 42,000 molecular weight, and 0.8 mg of magnesium stearate; a hydrogel, expandable layer comprising 37.80 mg of poly(ethylene oxide) possessing a 2,000,000 molecular weight, 30 mg of osmagent sodium chloride, 3 mg of hydroxypropylmethylcellulose of 9,200 molecular weight, 0.6 mg of red ferric oxide, and 0.15 mg of lubricant magnesium stearate; a semipermeable wall comprising 27.2 mg of cellulose acetate of 39.8% acetyl content, and 0.275 mg of polyethylene glycol of 3,350 molecular weight; a mean release rate of 0.427 mg/hr for 17.3 hours; and a 25 mil (0.635 mm) passageway; (B) a dosage form with a hydromorphone drug layer comprising 32 mg of hydromorphone hydrochloride, 119.6 mg of poly(ethylene oxide) possessing a 200,000 molecular weight, 8 mg of poly(vinyl pyrrolidone) of 42,000 molecular weight, and 0.4 mg of magnesium stearate; an expandable layer comprising 76.49 mg of hydrogel poly(ethylene oxide) of 2,000,000 molecular weight, 36 mg of osmagent sodium chloride, 6 mg of hydroxypropylmethyl cellulose of 9,200 molecular weight, 1.2 mg of red ferric oxide, and 0.012 mg of butylated hydroxytoluene antioxidant; a semipermeable wall comprising 29.6 mg of cellulose acetate comprising an acetyl content of 39.8%, and 0.29 mg of polyethylene glycol of 3,350 molecular weight; a hydromorphone controlled-release rate of 1.811 mg/hr for 16.1 hours; and a 25 mil (0.635 mm) passageway; (C) a dosage form comprising a hydromorphone drug layer comprising 64.0 mg of hydromorphone hydrochloride, 138.6 mg of poly(ethylene oxide) of 200,000 molecular weight, and 0.53 mg of lubricant magnesium stearate; a delivery layer comprising 104.533 mg of poly(ethylene oxide) of 2,000,000 molecular weight, 49.2 mg of osmagent sodium chloride, 8.2 mg of hydroxypropylmethylceliulose of 9,200 molecular weight, 1.64 mg of red ferric oxide colorant, 0.41 mg of magnesium stearate lubricant, and 0.0164 mg of antioxidant butylated hydroxytoluene; a semipermeable wall comprising 38.61 mg of cellulose acetate comprising a 39.8% acetyl content, and 0.39 mg of polyethylene glycol of 3,350 molecular weight; a controlled rate of release of 3.77 mg/hr over an extended period of 15.3 hours; and a 25 mil (0.635 mm) passageway for delivering the hydromorphone from the dosage form; and (D) a dosage form comprising 16 mg of hydromorphone hydrochloride, 135.6 mg of poly(ethylene oxide) of 200,000 molecular weight, 8 mg of poly(vinyl pyrrolidone) of 42,000 molecular weight, and 0.4 mg of lubricant magnesium stearate; a hydrogel delivery layer comprising 76.49 mg of poly(ethylene oxide) of 2,000,000 molecular weight, 36 mg of osmagent sodium chloride, 6 mg of hydroxypropylmethylcellulose, 1.2 mg of black ferric oxide colorant, 0.3 mg of magnesium stearate lubricant, 0.12 mg of antioxidant butylated hydroxytoluene; a semipermeable wall comprising 27.52 mg of cellulose acetate of 39.8% acetyl content, and 0.27 mg of polyethylene glycol of 3,350 molecular weight; a controlled release rate of 0.957 mg/hr for 15.0 hours; and a 25 mil (0.635 mm) passageway.

EXAMPLE 13

A dosage form is provided by following the above teachings, wherein the dosage form delivers 0.4 to 3.7 mg/hr at a controlled rate, over an extended time up to 24 hours, to provide hydromorphone to a patient in need of same.

EXAMPLE 14

The dosage form prepared according to Example 13, wherein the dosage form comprises 10 to 100 mg of hydromorphone.

EXAMPLE 15

A dosage form is provided by following the above disclosure, wherein the dosage form comprises 2 to 75 mg of hydromorphone that is administered over 24 hours to produce from greater than zero ng to 10 ng/ml of plasma, generally from 0.01 ng to 10 ng/ml, for producing a plasma hydromorphone concentration.

EXAMPLE 16

A dosage form adapted, designed and shaped as an osmotic drug delivery device is manufactured as follows: first, sublots of drug granulation were manufactured as follows: first, 2000 g of hydromorphone hydrochloride, 16,950 g of a pharmaceutically acceptable poly(ethylene oxide) comprising a 200,000 average molecular weight, 900 g of poly(vinyl-pyrrolidone) of 40,000 average molecular weight, are added to the bowl of a granulator, and the ingredients granulated to yield the granulation. Next, the dry granulated powders were all suspended and mixed thoroughly for three minutes. Then, a solution was prepared by dissolving 120 g of poly(vinylpyrrolidone) of 40,000 average molecular weight in 5,800 g of anhydrous ethyl alcohol and the solution sprayed onto the powder with mixing in a granulator bowl. The granulation is mixed for twenty minutes with constant addition of the solution. Then, the granulation is dried under vacuum to a moisture content of below 1.5%. The granulating conditions were as follows: a solution spray rate of 200 g/min; bowl temperature 25° C.; vacuum between 40 and 80 millibar. The granules were sized in a fluid air mill with a 7 mesh screen (2.81 mm). The screen are U.S. Series, in *Perry's Chemical Engineers' Handbook*, Sixth Edition, pp 21–15, Table 21–6, (1984).

Next, the granulation was transferred to a tumbler and lubricated with mixing with 142 of magnesium stearate.

Next, a push composition was prepared as follows: first, a binder solution is prepared by dissolving 4000 g of hydroxypropylmethylcellulose of 11,200 average molecular weight in 46,000 g of water. Then, 36,000 g of sodium chloride osmagent was sized in a mill equipped with a 21 mesh screen. Then, 1200 g of ferric oxide was passed through a 40 mesh screen. Then, all the screened materials, and 76,400 g of pharmaceutically acceptable poly(ethylene oxide) comprising a 2,000,000 molecular weight, 2516 g of hydroxypropylmethylcellulose comprising an 11,200 average molecular weight were added to a fluid bed granulator bowl, and the ingredients granulated to effect the process. The dry powders were an suspended next, and mixed for 10 minutes. Then, the binder solution was sprayed onto the powders at a rate of 700 g/min, at a temperature of 25° C., and at an air flow between 500 and 4000 m$^3$/hr.

Next, at the end of the solution spraying, 43,550 g of the granulated granules were dried for 20 minutes. Then, the granules were sized in a mill equipped with a 7 mesh screen. Then, the granulation was transferred to a tumbler and mixed with 88.2 g of butylated hydroxytoluene and then mixed with 294 g of magnesium stearate.

Next, the hydromorphone hydrochloride drug composition and the push composition were compressed into bilayered tablets on a tablet press. First, 80 mg of hydromorphone hydrochloride composition was added to a die cavity and pre-compressed. Then, 60 g of the push composition was added and the layers pressed under a pressure of 1200 pounds into a 9/32 inch (0.71 cm) round-contacting layered arrangement.

Next, the bilayered arrangements were coated with a semipermeable wall. The wall-forming composition comprises 99% cellulose acetate having a 39.8% acetyl content, and 1% polyethylene glycol having a 3350 molecular weight. The wall-forming composition was dissolved in an acetone: water (96:4 wt:wt) cosolvent to make a 4% solids solution. The wall-forming composition was sprayed onto and around the bilayers in a coater. Next, one 25 mil (0.635 mm) exit passageway was drilled through the semipermeable wall to connect the drug layer with the exterior of the dosage form. The residual solvent was removed by drying for 96 hours at 45° C. and 45% humidity. The dosage forms were dried at 4 hours at 45° C. to remove the moisture.

The dosage form produced by this manufacture provides 10% hydromorphone hydrochloride, 84.75% poly(ethylene oxide) possessing a 200,000 molecular weight, 5% poly (vinylpyrrolidone) possessing a 40,000 molecular weight and 0.25% magnesium stearate in the drug composition. The push composition comprises 63.675% poly(ethylene oxide) comprising a 2,000,000 molecular weight, 30% sodium chloride, 5% hydroxypropylmethylcellulose comprising a 11,200 molecular weight, 1% ferric oxide, 0.075% butylated hydroxytoluene and 0.25% magnesium stearate. The semipermeable wall comprises 99 wt % cellulose acetate comprising a 39.8% acetyl content, and 1% polyethylene glycol comprising a 3350 molecular weight. The dosage form comprises one passageway, 2.5 mils (0.635 mm), and the dosage form had a hydromorphone hydrochloride mean release rate of 0.5 mg/hr.

EXAMPLES 17 to 20

The procedure set forth in Example 16 was repeated to manufacture dosage forms as follows: (17) a dosage form comprising a drug layer of 80 mg comprising 8 mg of drug expressed as 10.5% hydromorphone hydrochloride, 84.23% polyethylene oxide of 200,000 molecular weight, 5% poly (vinylpyrrolidone of 40,000 molecular weight and 0.25% of magnesium stearate; (18) a dosage form comprising a drug layer of 160 mg comprising 16 mg of hydromorphone hydrochloride, expressed in percent as 10% hydromorphone hydrochloride, 84.75% poly(ethylene oxide) of 200,000 molecular weight, and 5% poly(vinylpyrrolidone of 40,000 molecular weight, and 0.25% magnesium stearate; (19) a dosage form comprising a 160 mg drug layer comprising 32 mg of hydromorphone hydrochloride expressed as 20% hydromorphone hydrochloride, 74.75% poly(ethylene oxide) of 200,000 molecular weight, 5% poly (vinylpyrrolidone) of 40,000 molecular weight, and 0.25% of magnesium stearate; and (20) a dosage form comprising a drug composition of 214 mg comprising 64 mg of hydromorphone with the total drug composition comprising 30% hydromorphone, 64.75% poly(ethylene oxide) of 200,000 molecular weight, 5% poly(vinylpyrrolidone) of 40,000 molecular weight, and 0.25% magnesium stearate.

The push layer for the dosage forms of Examples 17, 18, 19, and 20 weighted 60, 120, 120 and 164 mg respectively. The push layers of Examples 17, 18, 19 and 20 comprise 64.3% poly(ethylene oxide of 2,000,000 molecular weight, 30% sodium chloride, 5% hydroxypropylmethylcellulose of 11,200 molecular weight, 0.075% butylated hydroxytoluene, 1% ferric oxide, and 0.25% magnesium stearate.

The semipermeable wall for the dosage forms of Examples 17, 18, 19 and 20 comprises 99% cellulose acetate of 39.8% acetyl content and 1% polyethylene glycol of 3350 molecular weight. The dosage form comprise a 25 mil push composition as expressed in weight %. The dosage form optionally comprise a color overcoat, white, yellow, blue or red.

DISCLOSURE FOR USING THE INVENTION

The invention also concerns a method for administering 1 to 500 mg of hydromorphone to a patient in need of pain relief. The method, in one administration, comprises admitting orally into the patient 1 to 500 mg of a hydromorphone selected from the group consisting of hydromorphone base or hydromorphone salt that is administered from a therapeutic composition, or from a dosage form in an extended-release profile for a 16 mg, a 32 mg or 64 mg total dose of 0 to 20% in 0 to 4 hrs, 20 to 50% in 0 to 8 hrs, 55 to 85% in 0 to 14 hrs, and 80 to 100% in 0 to 24 hrs and for an 8 mg dosage form, no more than 20 to 50% in 0 to 8 hrs, no more than 55 to 85% in 0 to 14 hrs, and no less than 75 to 100% in 0 to 24 hrs.

The invention also concerns a method for administering 1 to 500 mg of hydromorphone to a patient. The method comprises admitting orally 1 to 500 mg of hydromorphone to the patient, which is administered from a dosage form comprising a semipermeable wall permeable to aqueous-biological fluid and impervious to the passage of hydromorphone. The semipermeable wall surrounds an internal space or compartment comprising a hydromorphone drug composition and a push composition. The hydromorphone drug composition comprises 1 to 500 mg of hydromorphone, 20 to 375 mg of poly(alkylene oxide) having a 50,000 to 750,000 molecular weight, 0.01 to 25 mg of poly (vinylpyrrolidone) having a 5,000 to 350,000 molecular weight, and 0 to 10 mg of a lubricant. The push composition comprises 20 to 375 mg of a hydrogel polymer, such as a poly(alkylene oxide) of 1,000,000 to 10,000,000 molecular weight, 0 to 75 mg of an osmagent, 0 to 75 mg of hydroxyalkylcellulose, 0.01 to 5.5 mg of a colorant, 0.01 to 10 mg of a lubricant, and 0 to 10 mg of an antioxidant; and exit means in the semipermeable wall for delivering the hydromorphone from the dosage form by imbibing fluid through the semipermeable wall into the dosage form, causing the hydromorphone composition to become dispensable and causing the push composition to expand and push the hydromorphone composition through the exit, whereby, through the combined operations of the dosage form, the hydromorphone is delivered at a therapeutically effective dose at a controlled rate over a sustained period of time.

A clinical pharmacokinetic study was performed on healthy subjects to ascertain the therapeutic benefits obtained by administering hydromorphone from a controlled, extended-release dosage form provided by this invention, compared to the therapeutic benefits obtained by administering hydromorphone from an immediate-release dosage form. The study evaluated both the single- and multiple-dose pharmacokinetics of hydromorphone and its metabolite following oral administration of hydromorphone. The dosing form of this invention was compared to an immediate-release dosage form, dosing for four days.

The profile of the clinical study compared randomized, cross-over doses using 18 healthy volunteers consisting of both male and female patients. The controlled-extended release dosage form provided by the invention was used to administer a 16-mg dose of hydromorphone orally at 8:00 AM for four days. The immediate-release dosage form was used to administer 4 mg of hydromorphone orally every six hours at 8:00 AM, 2:00 PM, 8:00 PM, and 2:00 AM daily for four days. There was a washout period of at least three days between the two treatments.

The administration of hydromorphone by the osmotic dosage form provided by the invention was followed by the collection of venous blood samples for pharmacokinetic profile determinations on day one and for 48 hours after the day-four dosing period. The administration of hydromorphone by an immediate-release dosage form was followed by the collection of venous blood samples for pharmacokinetic profile determinations for 48 hours after the day-four dosing period. The immediate-release dosing form used in the clinical studies comprised a solid tablet consisting of 4 mg of hydromorphone, yellow dye, lactose and magnesium stearate, available by prescription as Dilaudid® hydromorphone. *The Physician's Desk Reference*, 50$^{th}$ Ed., pp. 1335–1337 (1996).

The clinical samples were analyzed for hydromorphone parameters, including area under the curve, maximum concentration, minimum concentration and concentration average for the two distinctly different hydromorphone treatments. The results of the clinical studies are presented in the accompanying figures.

Figure 5:
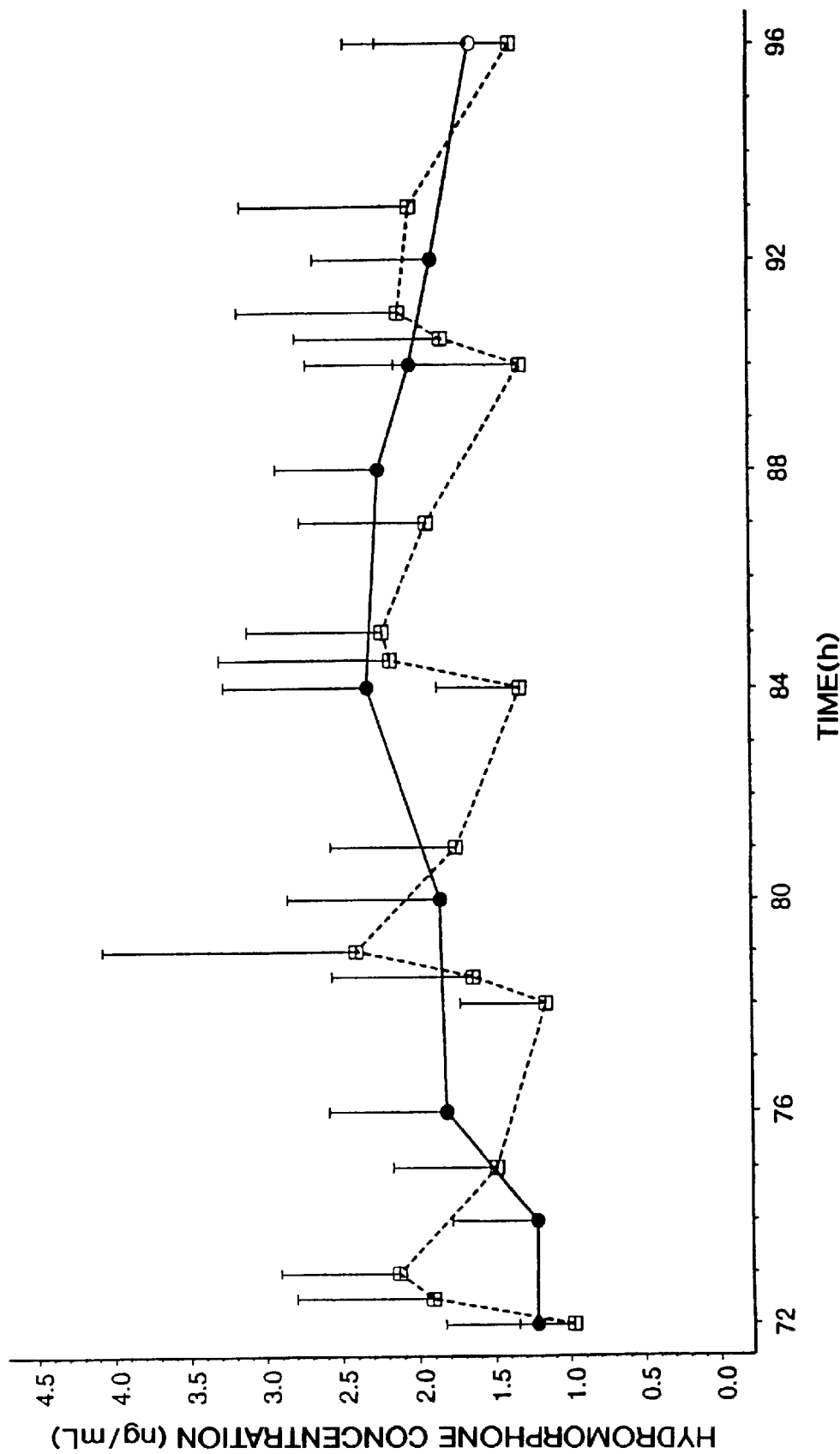
FIG. 5 depicts the mean plasma hydromorphone concentration profile for hydromorphone.

FIG. 5 depicts the mean plasma hydromorphone concentration profiles for hydromorphone treatment on days four and five. The osmotically controlled extended-release dosage form results are illustrated by the solid line with black circles. This dosage form was administered once-a-day, and it comprised 16 mg of hydromorphone. The dashed line with clear squares in FIG. 5 depicts plasma profile for the immediate-release dosage form administered four-times-a-day, which comprised 4 mg per immediate-release dosage form.

Figure 6:
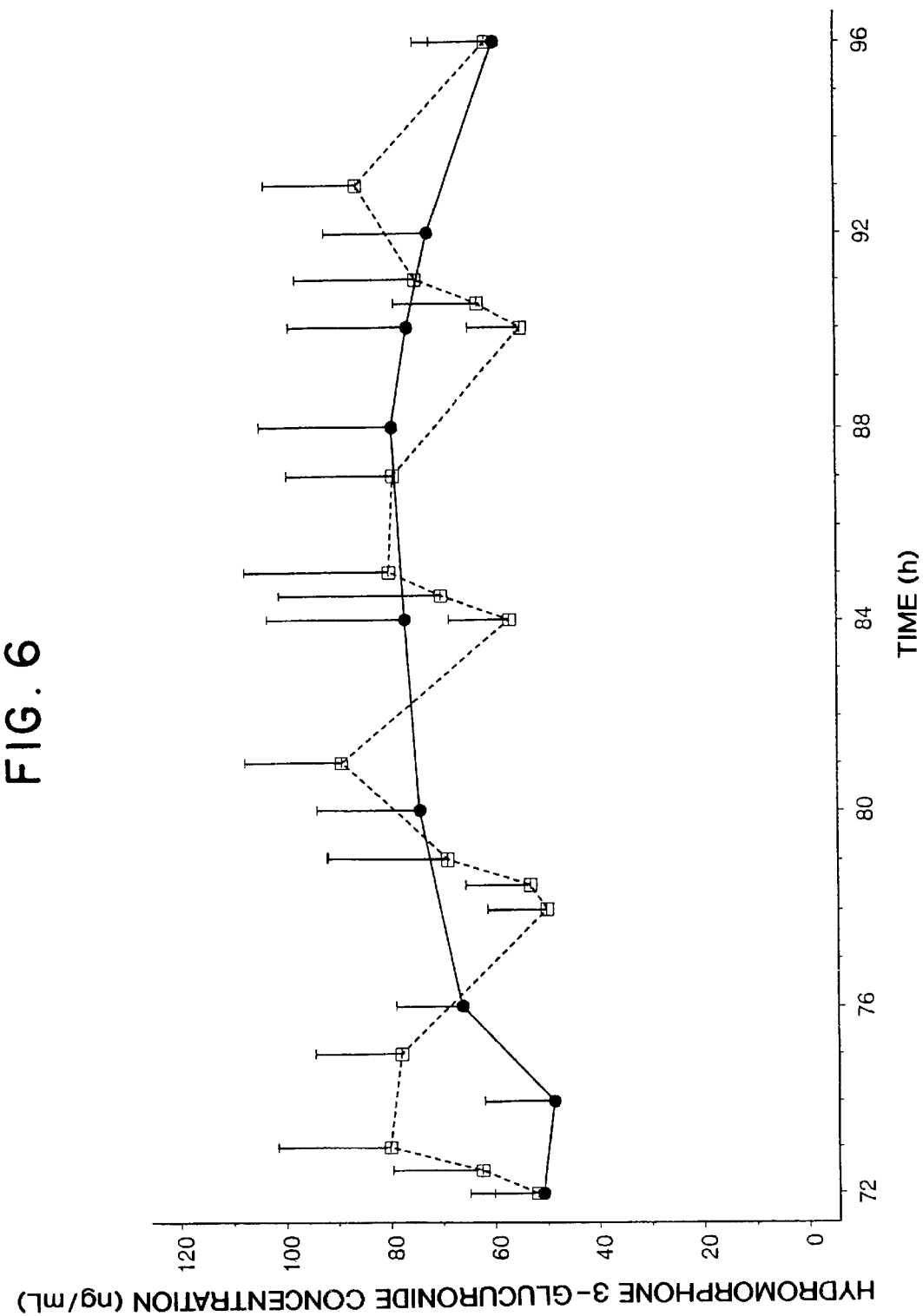
FIG. 6 depicts the mean plasma hydromorphone 3-glucuronide concentration following hydromorphone treatment; and Drawing

FIG. 6 depicts the mean plasma hydromorphone 3-glucuronide concentration following hydromorphone treatment on days four and five. In FIG. 6, the solid line with black circles denotes the plasma profile for the invention's osmotic dosage form administered once-a-day, which comprised 16 mg of hydromorphone. The dashed lines with clear squares denote the plasma profile for the immediate-release tablet orally administered four-times-a-day, which comprised 4 mg for each administration.

Figure 7:
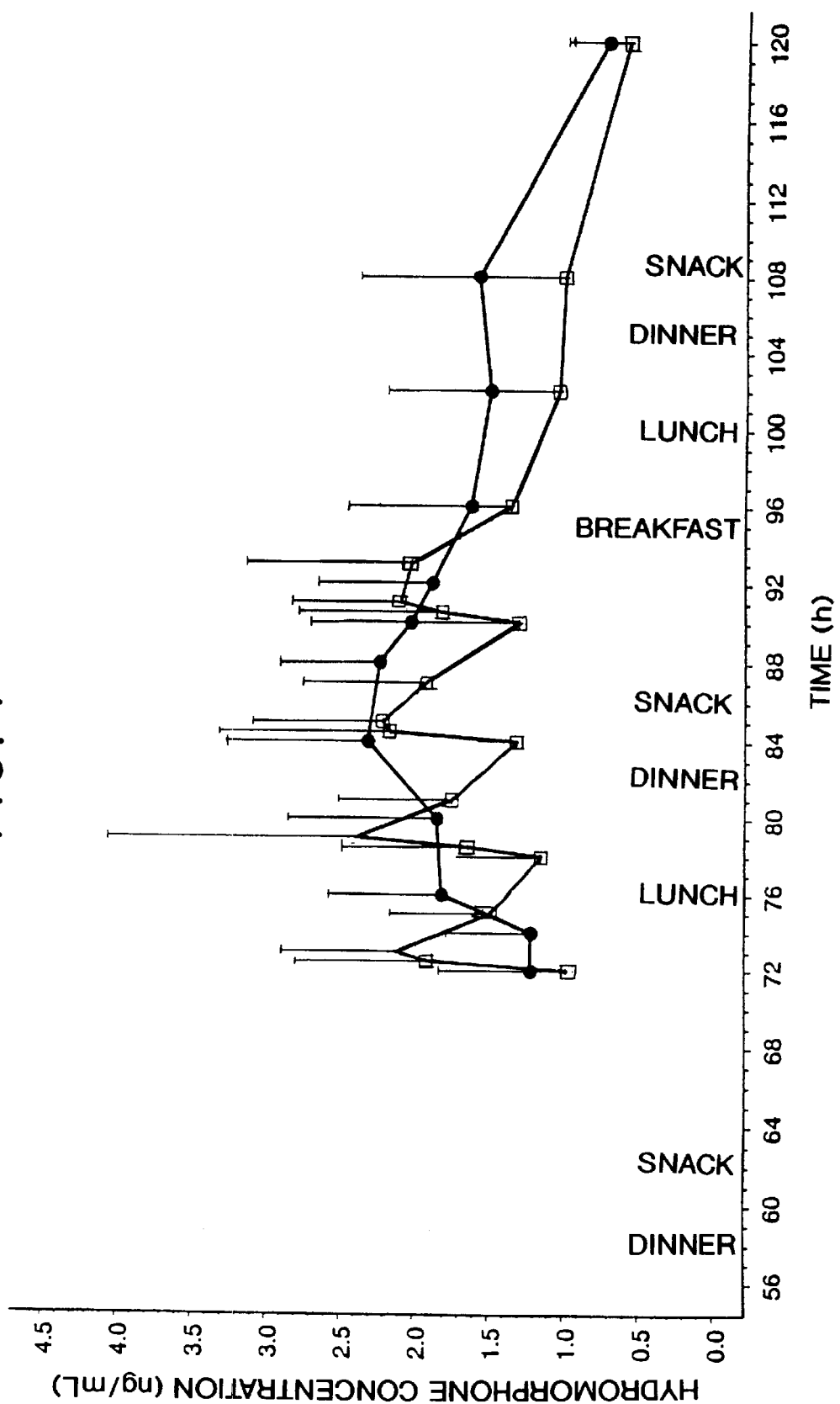
FIG. 7 depicts the mean plasma hydromorphone concentration profile for hydromorphone treatment.

FIG. 7 depicts the mean plasma hydromorphone concentration profiles for hydromorphone treatment on day four, determined at mealtime. The solid line with black circles in this figure illustrates the clinical picture effected by oral administration once-a-day of a 16 mg controlled-extended release dosage form. The solid line with clear squares, in this figure, illustrates the clinical picture effected by oral administration four-times-a-day of a 4 mg immediate-release dosage form. The mean steady state hydromorphone data for 18 subjects is for the immediate-release form administered four-times-a-day, with 4 mg each time, a plasma concentration maximum of 3.4 ng/mil with 10.1 hours to reach the maximum concentration, a plasma concentration minimum of 0.9 ng/ml with 6.4 hours to reach the concentration minimum, and an area under the curve of 41.2 ng-hr/ml. The mean steady state hydromorphone data for 18 subjects is for the osmotic dosage form administered once-a-day with a dose of 16 mg, a plasma concentration maximum of 2.6 ng/ml with 14.7 hours to reach the maximum concentration, a plasma concentration minimum of 1.2 ng/ml with 13.1 hours to reach the minimum concentration, and an area under the curve of 44.8 ng-hr/ml.

The invention provides methods for administering hydromorphone to a patient, and methods for producing a plasma concentration of hydromorphone. The method of the invention provides for admitting orally to a patient a dosage form that administers at a controlled rate, over a continuous time up to 24 hours, hydromorphone for its intended therapy. The method also comprises administering orally to a patient a therapeutic dose of hydromorphone from a single dosage form that administers the hydromorphone over 24 hours. The method of the invention further comprises administering hydromorphone for producing a first hydromorphone concentration in the plasma, a second, elevated hydromorphone concentration in the plasma, and a third, continuous hydromorphone concentration in the plasma.

The method of the invention also comprises administering hydromorphone for producing a first plasma hydromorphone concentration in from 0 to 8 hours, a second, elevated plasma hydromorphone concentration in 8 to 12 hours, and a third, continuous plasma hydromorphone concentration over 12 to 24 hours. The method provides pain relief in a patient in need of pain relief. The method further provides a plasma concentration of hydromorphone in a patient in need of hydromorphone comprising orally administering to the patient a dosage form that provides a controlled rate of extended administration of from 1 to 65 mg of hydromorphone over a period of time up to 24 hours for producing from greater than zero ng, including 0.01 ng, to 10 ng/ml of plasma hydromorphone in a human patient.

Figure 8:
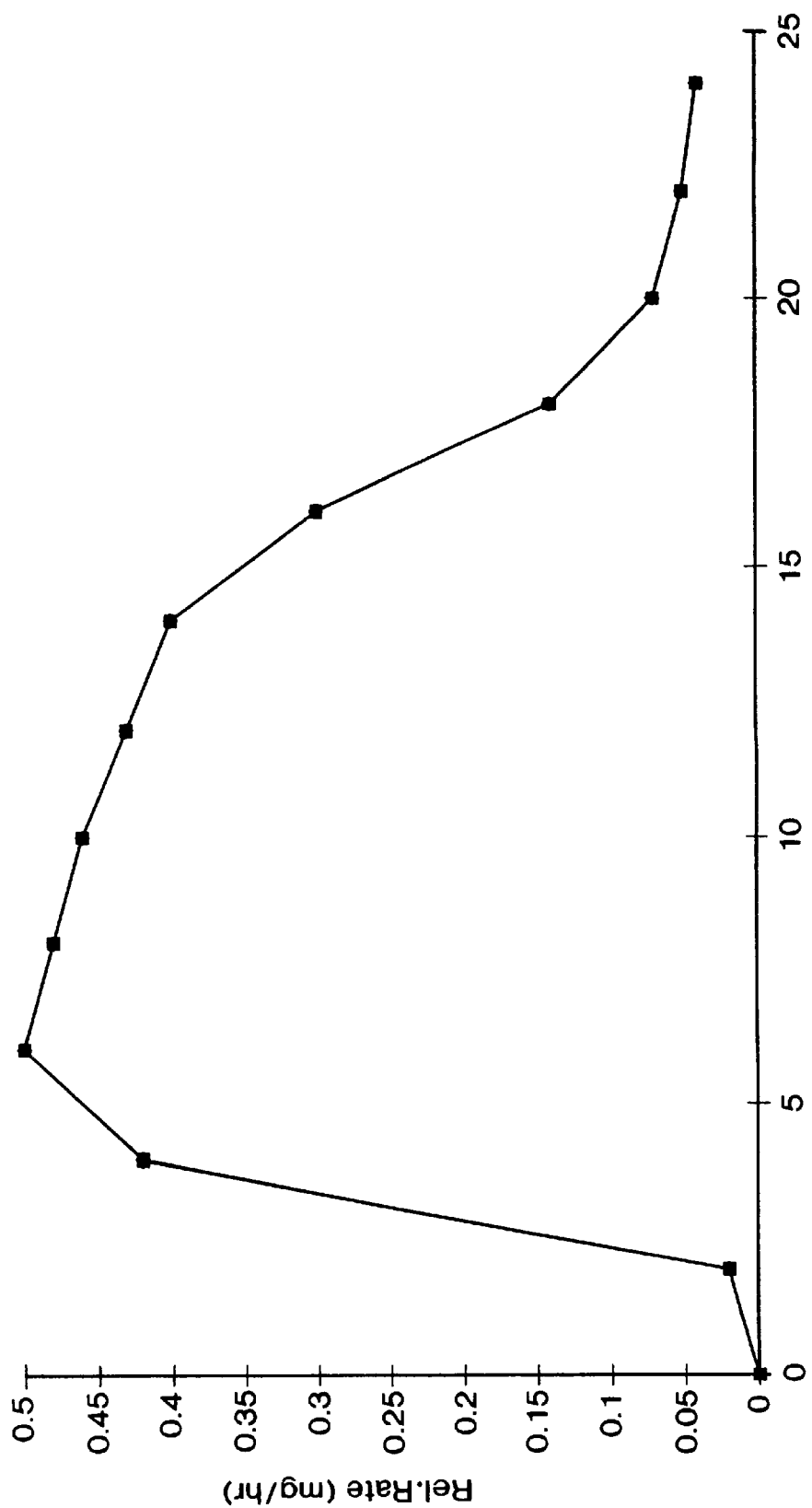
FIGS. 8 to 12 depict release rate patterns and clinical data provided by the invention.
Figure 9:
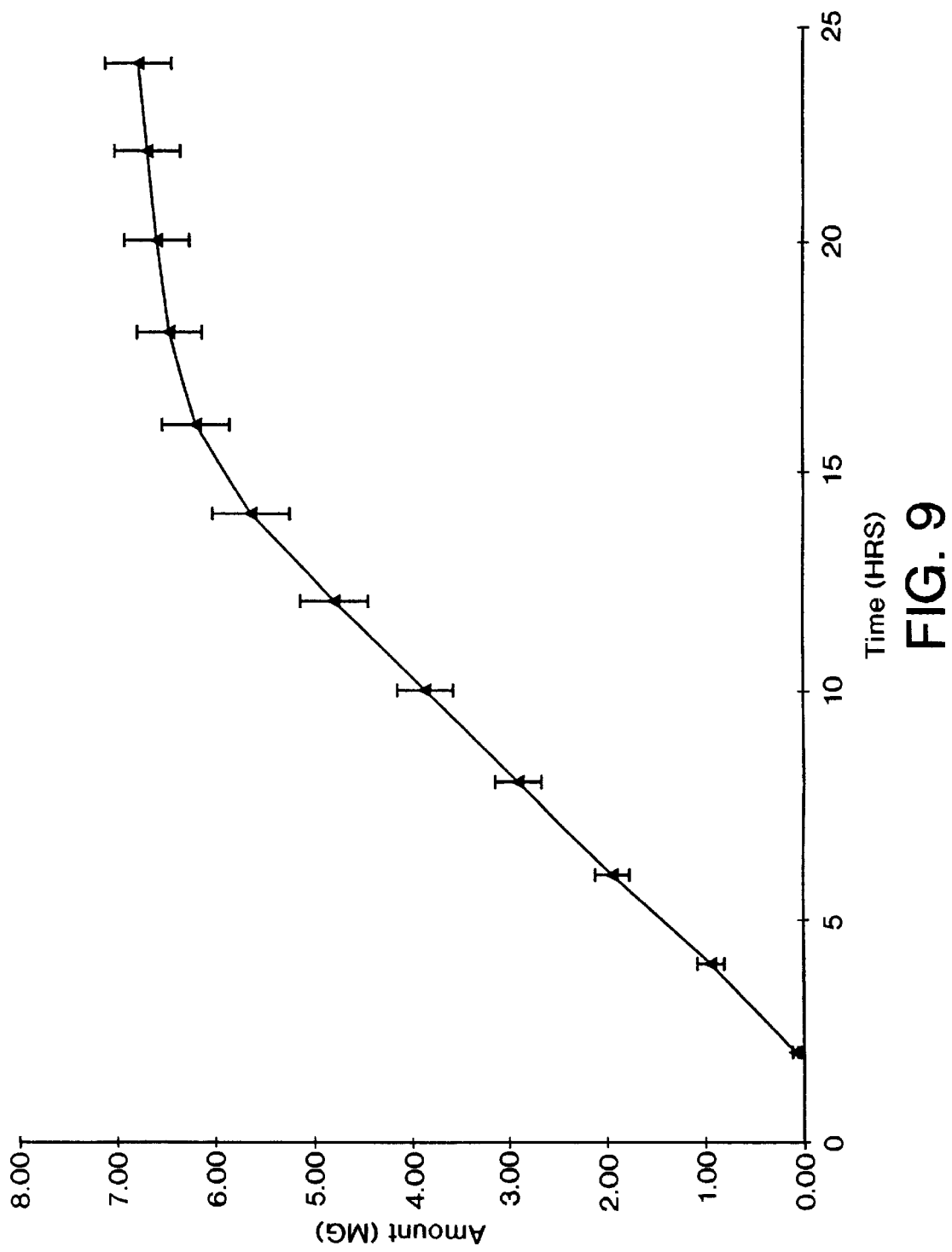
Figure 10:
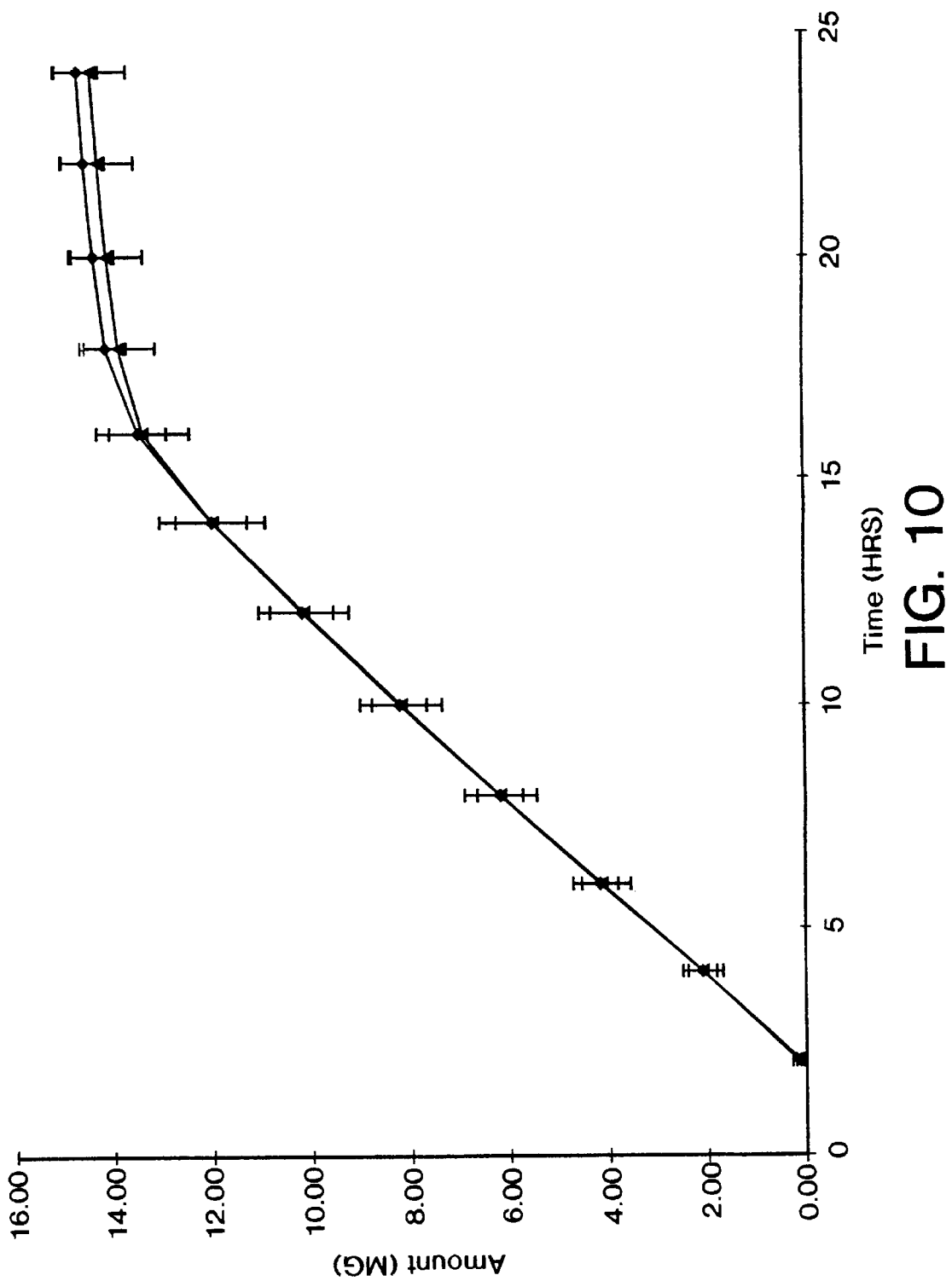
Figure 11:
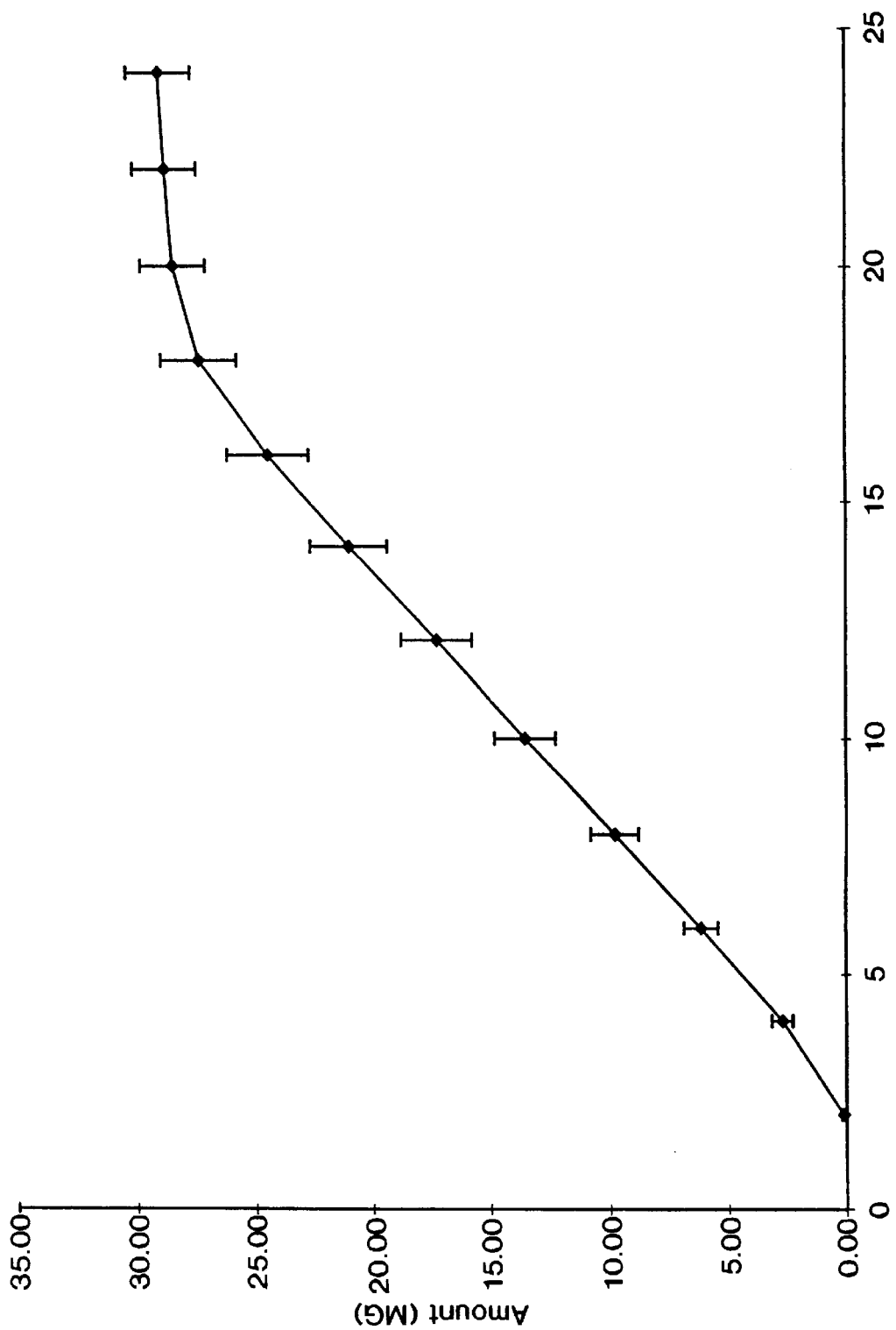
Figure 12:
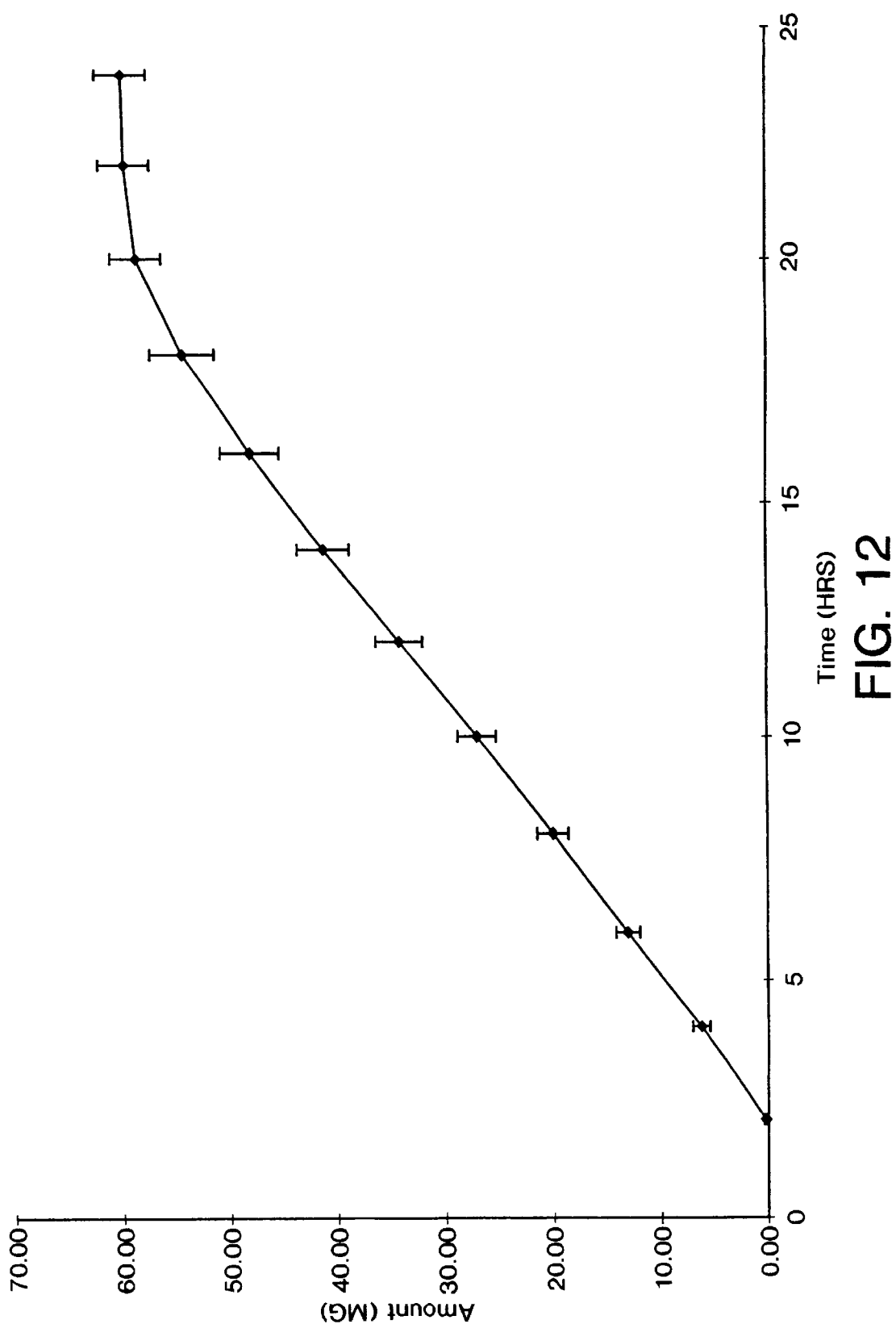

Further data that support the unexpected results provided by the invention are seen in the accompanying figures, wherein FIG. 8 depicts the area under a curve for a dosage form comprising 8 mg of hydromorphone, FIG. 9 depicts the cumulative dose released from 8 mg dosage form over 25 hrs, FIG. 10 depicts the cumulative dose release from a 16 mg dosage form over 25 hrs, FIG. 11 illustrates the cumulative dose release from a 32 mg dosage form over 25 hrs, and FIG. 12 illustrates the cumulative dose release from a 64 mg dosage form over 25 hrs.

In as much as the foregoing specification comprises disclosed embodiments, it is understood what variations and modifications may be made herein, in accordance with the principles disclosed, without departing from the invention.

We claim:

1. A dosage form comprising a drug layer comprising 8 mg of hydromorphone, 67.8 mg of poly(ethylene oxide) of 200,000 molecular weight, 4 mg of poly(vinyl pyrrolidone), and 0.2 mg of a lubricant; a delivery layer comprising 37.8 mg of poly(ethylene oxide) possessing a 2,000,000 molecular weight, 18 mg of sodium chloride, 3 mg of hydroxypropylmethyl) cellulose of 9,200 molecular weight, 0.6 mg of a colorant, and 0.15 mg of a lubricant; a semipermeable wall comprising 27.2 mg of cellulose acetate of 39.8% acetyl content, and 0.275 mg of polyethylene glycol of 3,350 molecular weight; a passageway in the wall; and a controlled rate of release of 0.427 mg/hr for 17.3 hours.

2. A dosage form comprising 32 mg of hydromorphone, 119.6 mg of poly(ethylene oxide) possessing a 200,000 molecular weight, 8 mg of poly(vinyl pyrrolidone) of 42,000 molecular weight, and 0.4 mg of magnesium stearate; a delivery layer comprising 76.49 mg of poly(ethylene oxide) of 2,000,000 molecular weight, 36 mg of sodium chloride, 6 mg of hydroxypropylmethylcellulose of 9,200 molecular weight, 0.3 mg of magnesium stearate, 1.2 mg of a colorant, and 0.012 mg of an antioxidant; a semipermeable wall comprising 29.6 mg of cellulose acetate comprising an acetyl content of 39.8%, and 0.29 mg of polyethylene glycol possessing a 3,350 molecular weight, which wall surrounds the layers; a passageway in the dosage form; and a controlled rate of release of 1.811 mg/hr for 16.1 hours.

3. A dosage form comprising 64 mg of hydromorphone, 138.6 mg of poly(ethylene oxide) possessing a 200,000 molecular weight, 10.7 mg of poly(vinyl pyrrolidone) of 42,000 molecular weight, and 0.53 mg of a lubricant; a delivery layer comprising 104.53 mg of poly(ethylene oxide) of 2,000,000 molecular weight, 49.2 mg of an osmagent, 8.2 mg of hydroxypropylmethylcellulose of 9,200 molecular weight, 1.64 mg of a colorant, 0.41 mg of a lubricant, and 0.123 mg of an antioxidant; a semipermeable wall comprising 38.61 mg of cellulose acetate comprising a 39.8% acetyl content, and 0.39 mg of polyethylene glycol of 3,350 molecular weight, which wall surrounds the layers; a passageway in the wall; and a controlled rate of release of 3.77 mg/hr of hydromorphone over 15.3 hours.

4. A dosage form comprising 16 mg of hydromorphone, 135.6 mg of poly(ethylene oxide) of 200,000 molecular weight, 8 mg of poly(vinyl pyrrolidone) of 42,000 molecular weight, and 0.4 mg of a lubricant; a delivery layer comprising 76.49 mg of poly(ethylene oxide) of 2,000,000 molecular weight, 36 mg of an osmagent, 6 mg of hydroxypropylmethylcellulose of 9,200 molecular weight, 1.2 mg of a colorant, 0.3 mg of a lubricant, and 0.12 mg of an antioxidant; a semipermeable wall that surrounds the layers comprising 27.52 mg of cellulose acetate of 39.8% acetyl content, and 0.27 mg of polyethylene glycol of 3,350 molecular weight; a passageway in the dosage form; and a controlled rate of release of 0.957 mg/hr for 15.0 hours.

5. A dosage form comprising: a drug layer comprising 8 mg of a member selected from the group consisting of hydromorphone and hydromorphone pharmaceutically acceptable salt, 84.70 wt % poly(ethylene oxide), 5 wt % poly (vinylpyrrolidone), 0.05 wt % butylated hydroxytoluene and 0.25 wt % magnesium stearate; an expandable layer comprising 63.675 wt % poly(ethylene oxide), 30 wt % of sodium chloride, 5 wt % of hydroxypropylmethylcellulose, 0.075 wt % of butylated hydroxytoluene, 1 wt % of a colorant, and 0.25 wt % of magnesium stearate; a semipermeable wall comprising 99 wt % cellulose acetate and 1 wt % polyethylene glycol that surrounds the drug and expansion layers; and, an exit in the wall for delivering hydromorphone from the dosage form.

6. The dosage form according to claim 5, wherein the drug layer comprises 16 mg of a member selected from the group consisting of hydromorphone and a pharmaceutically acceptable salt.

7. The dosage form according to claim 5, wherein the drug layer weighs 80 mgs.

8. The dosage form according to claim 6, wherein the drug layer weighs 160 mg.

9. The dosage form according to claim 5, wherein the expandable layer weighs 60 mg.

10. The dosage form according to claim 6, wherein the expandable layer weighs 120 mg.

11. The dosage form according to claim 5, wherein the dose of hydromorphone comprises 10 wt % of the drug layer.

12. The dosage form according to claim 6, wherein the dose of hydromorphone comprises 10 wt % of the drug layer.

13. A dosage form comprising: a drug layer comprising 32 mg of a member selected from the group consisting of hydromorphone and hydromorphone pharmaceutically acceptable salt, 74.75 wt % poly(ethylene oxide), 5 wt % poly(vinylpyrrolidone) and 0.25 wt % magnesium stearate, an expandable layer comprising 63.675 wt % poly(ethylene oxide), 30 wt % sodium chloride, 5 wt % hydroxypropylmethylcellulose, 0.075 butylated hydroxytoluene, 1 wt % colorant, and 0.25 wt % magnesium stearate; a semipermeable wall comprising 99 wt % cellulose acetate and 1 wt % poly(ethylene glycol), which wall surrounds the drug and expandable layers; and, an exit in the wall for delivering hydromorphone from the dosage form.

14. The dosage form according to claim 13, wherein the drug layers weighs 160 mg.

15. The dosage form according to claim 13, wherein the expandable layer weighs 120 mg.

16. The dosage form according to claim 13, wherein the dose of hydromorphone is 20 wt % of the drug layer.

17. A dosage form for delivering orally hydromorphone to a patient in need of relief from pain, wherein the dosage form comprises: a drug layer comprising 64 mg of a member selected from the group consisting of hydromorphone and its pharmaceutically acceptable salt, 64.75 mg of a poly (alkylene oxide), 5 wt % of a poly(vinylpyrrolidone) and 0.25 wt % of a lubricant; an expandable layer comprising 63.675 wt % of a poly(alkylene oxide), 30 wt % of an osmotically effective solute, 5 wt % of a hydroxypropylalkylcellulose, 0.075 wt % of an antioxidant, 1 wt % of a colorant, and 0.25 wt % of a lubricant; a semipermeable wall that surrounds the layers comprising 99 wt % cellulose acetate, and 1 wt % poly(ethylene glycol); and, an exit in the semipermeable wall for delivering the hydromorphone to the patient to provide relief from pain.

18. The dosage form according to claim 17, wherein the drug layer weighs 214 mg.

19. The dosage form according to claim 17, wherein the expandable layer weighs 164 mg.

20. The dosage form according to claim 17, wherein the dose of hydromorphone is 30 wt % of the drug layer.

21. A dosage form comprising a drug layer that weighs 80 mg and comprises 10.5% hydromorphone hydrochloride, 84.23% poly(ethylene oxide) having a 200,000 molecular weight, 5% poly(vinylpyrrolidone), 0.02% butylated hydroxytoluene, and 0.25% magnesium stearate; an expandable layer that weighs 60 mg and comprises 64.3% poly (ethylene oxide) possessing a 2,000,000 molecular weight, 30.00% sodium chloride, 5% hydroxypropylmethylcellulose, black iron oxide and lactose, 0.25% magnesium stearate, and 0.05 butylated hydroxytoluene; a membrane that surrounds the drug and expandable layers comprising 99% cellulose acetate and 1% polyethylene glycol; and an exit in the membrane for delivering the hydromorphone from the dosage form.

22. The dosage form according to claim 21, wherein the dosage form comprises 0.4% or 1% of black iron oxide and lactose.

23. The dosage form according to claim 21 on, wherein the poly(vinylpyrrolidone) comprises a molecular weight of 38,000 to 42,000, the hydroxypropylmethylcellulose comprises a molecular weight of 9,200 to 11,300, and the expandable layer weighs 54 to 66 mg.

24. The dosage form according to claim 21 wherein the cellulose acetate comprises a 39.8% acetyl content and the polyethylene glycol comprises a 3,350 to 4,000 molecular weight.

25. The dosage form according to claim 21, wherein the membrane is a wall and weighs 25 mg.

26. A dosage form comprising a drug layer that weighs 152.4 mg and comprises 10.5% hydromorphone hydrochloride, 84.23% poly(ethylene oxide) of 200,000 molecular weight, 5% poly(vinylpyrrolidone), 0.02% butylated hydroxytoluene, and 0.25% magnesium stearate; an expandable layer comprising 64.3% poly (ethylene oxide) possessing a 2,000,000 molecular weight, 30.00% sodium chloride, 5% hydroxypropylmethylcellulose, black iron oxide and lactose, 0.25% magnesium stearate, and 0.05% butylated hydroxytoluene; a membrane that surrounds the layer and comprises 99% cellulose acetate and 1% polyethylene glycol; and an exit in the membrane for delivering the drug from the dosage form.

27. The dosage form according to claim 26, wherein the dosage form comprises 0.4% or 1% of black iron oxide and lactose.

28. The dosage form according to claim 26, wherein the poly(vinylpyrrolidone) comprises a 38,000 to 42,000 molecular weight, the hydroxypropylmethylcellulose comprises a 9,200 to 11,300 molecular weight, and the expandable layer weighs 122 to 134 mg.

29. The dosage form according to claim 26 wherein, the cellulose acetate comprises a 39.8% acetyl content, and the polyethylene glycol comprises a 3,350 to 4,000 molecular weight.

30. The dosage form according to claim 26, wherein the membrane is a semipermeable wall and weighs 27 mg.

31. The dosage form according to claim 26, wherein the black iron oxide and the lactose are present as a 95:5 mix.

32. A dosage form comprising a drug layer that weighs 160 mg and comprises 20% hydromorphone hydrochloride, 74.68% poly(ethylene oxide) possessing a 200,000 molecular weight, 5% poly(vinylpyrrolidone), 0.02% butylated hydroxytoluene, and 0.25% magnesium stearate; an expandable layer comprising 63.672% poly(ethylene oxide) possessing a 2,000,000 molecular weight, 30.00% sodium chloride, 5% hydroxypropylmethylcellulose, 1% black iron oxide and lactose, 0.25% magnesium stearate, and 0.05% butylated hydroxytoluene; a rate controlling membrane that surrounds both layers and comprises 99% cellulose acetate and 1% polyethylene glycol; and an exit in the membrane for delivering the drug from the dosage form.

33. The dosage form according to claim 32 wherein, the drug layer comprises 0.05% ferric oxide yellow.

34. The dosage form according to claim 32 wherein, the poly(vinylpyrrolidone) possesses a 38,000 to 42,000 molecular weight, the hydroxypropylmethylcellulose comprises a 9,200 to 11,300 molecular weight, and the expandable layer weighs 114 to 126 mg.

35. The dosage form according to claim 32 wherein, the cellulose acetate comprises an acetyl content of 39.8% and the polyethylene glycol comprises a 3,350 to 4,000 molecular weight.

36. The dosage form according to claim 32 wherein, the membrane is a semipermeable wall and weighs 29 mg.

37. The dosage form according to claim 32 wherein, the black iron oxide and lactose comprise a 95:5 mix and is a colorant.

38. A dosage form comprising a drug layer that weighs 213.3 mg and comprises 30% hydromorphone hydrochloride, 64.73% poly(ethylene oxide) possessing a 200,000 molecular weight, 5% poly(vinylpyrrolidone), 0.02% butylated hydroxytoluene and 0.25% magnesium stearate; an expandable layer comprising 64.3% poly (ethylene oxide) possessing a 2,000,000 molecular weight, 30.003% sodium chloride, 5% hydroxypropylmethylcellulose, black iron oxide and lactose, 0.25% magnesium stearate, and 0.05% butylated hydroxytoluene; a membrane that surrounds the layers and comprises 99% cellulose acetate and 1% polyethylene glycol; and an exit in the membrane for delivering the hydromorphone from the dosage form.

39. The dosage form according to claim 38, wherein the dosage form comprises 0.4% or 1% black iron oxide and 0.05% butylated hydroxytoluene.

40. The dosage form according to claim 38 wherein, the poly(vinylpyrrolidone) comprises a 38,000 to 42,000 molecular weight, the hydroxypropylmethylcellulose comprises a 9,200 to 11,300 molecular weight, and the expandable layer weighs 156 to 172 mg.

41. The dosage form according to claim 38 wherein, the cellulose acetate comprises an acetyl content of 39.8% and the polyethylene glycol comprises a 3,350 to 4,000 molecular weight.

42. The dosage form according to claim 38 wherein, the membrane is a semipermeable wall and weighs 40 mg.

43. The dosage form according to claim 38 wherein the black iron oxide and the lactose comprise a 95:5 mix, and is a colorant.

44. An extended-release pharmaceutical formulation comprising 1 mg to 500 mg of a total dose of a member selected from the group consisting of hydromorphone and hydromorphone pharmaceutically acceptable salt in a pharmaceutically acceptable carrier in a delivery dose pattern of from 0 to 20% in 0 to 4 hrs, 20 to 50% in 0 to 8 hrs, 55 to 85% in 0 to 14 hrs, and 80 to 100% in 0 to 24 hrs for achieving a therapeutically effective blood level over the delivery pattern.

45. A method for producing hydromorphone therapy in a patient, wherein the method comprises administering orally to the patient an extended-release pharmaceutical formulation comprising 1 mg to 500 mg of a member selected from the group consisting of hydromorphone and a hydromorphone pharmaceutically acceptable salt in a pharmaceutically acceptable carrier in a delivery dose pattern of from 0 to 20% in 0 to 4 hrs, 20 to 50% in 0 to 8 hrs, 55 to 85% in 0 to 14 hrs, and 80 to 100% in 0 to 24 hrs that produces a first plasma hydromorphone concentration, a second elevated plasma hydromorphone concentration, and a third continuous plasma hydromorphone concentration for producing hydromorphone therapy up to 24 hrs in the patient.

46. A method for providing a plasma concentration of hydromorphone in a patient, wherein the method comprises administering orally into gastrointestinal tract of the patient an extended-release pharmaceutical formulation comprising 1 mg to 500 mg of a member selected from the group consisting of hydromorphone and hydromorphone pharmaceutically acceptable salt in a pharmaceutically acceptable carrier that is delivered in from 0 to 20% in 0 to 4 hrs, 20 to 50% in 0 to 8 hrs, 55 to 85% in 0 to 14 hrs, and 80 to 100% in 0 to 24 hrs to produce from greater than zero ng/ml to twenty-five ng/ml plasma concentration of hydromorphone for up to 24 hrs of hydromorphone therapy.

* * * * *